(12) United States Patent
Zhang

(10) Patent No.: US 6,303,314 B1
(45) Date of Patent: Oct. 16, 2001

(54) T-CELL RECEPTOR Vβ-Dβ-Jβ SEQUENCE AND METHODS FOR ITS DETECTION

(75) Inventor: Jingwu Z. Zhang, Missouri City, TX (US)

(73) Assignee: Baylor College of Medicine, Houston, TX (US)

( * ) Notice: Subject to any disclaimer, the term of this patent is extended or adjusted under 35 U.S.C. 154(b) by 0 days.

(21) Appl. No.: 09/507,819

(22) Filed: Feb. 22, 2000

Related U.S. Application Data

(60) Provisional application No. 60/121,311, filed on Feb. 23, 1999.

(51) Int. Cl.[7] ............................. C12Q 1/68; C07H 21/02; C07H 21/04; C12N 15/00
(52) U.S. Cl. ............................. 435/6; 536/23.1; 536/24.3; 935/76; 935/77; 935/78
(58) Field of Search ................................. 536/23.1, 24.3; 435/6, 91.2; 935/76, 77, 78

(56) References Cited

U.S. PATENT DOCUMENTS

| | | | |
|---|---|---|---|
| 5,198,537 | 3/1993 | Huber et al. | 530/406 |
| 5,614,192 | 3/1997 | Vandenbark | 424/185.1 |

FOREIGN PATENT DOCUMENTS

| | | |
|---|---|---|
| WO 93/12814 | 7/1993 | (WO) . |
| WO 95/34320 | 12/1995 | (WO) . |

OTHER PUBLICATIONS

Saiki et al., Nature 324: 163–166 (1988).*
Vandenbark A.A. et al. "Immunization with a synthetic T–cell receptor V–region peptide protects against experimental autoimmune encephalomyelitis" *Nature* 341: 541–544 (1989).
Howell M.D. et al. "Vaccination against experimental allergic encephalomyelitis with T cell receptor peptides" *Science* 246:668–670 (1989).
Offner H. et al. "T cell receptor peptide therapy triggers autoregulation of experimental encephalomyelitis" *Science* 251:430–432 (1991).
Vandenbark A.A. et al. "Treatment of multiple sclerosis with T–cell receptor peptides: Results of a double–blind pilot trial" *Nature Medicine* 2:1109–1115 (1996).
International Search Report (Mailed Jun. 12, 2000).
Boehringer Mannheim Corporation. Boehringer Mannheim Biochemicals 1993 Catalog, p. 87.
Hong, J. et al., "A common TCR V–D–J Sequence in Vβ13.1 T Cells Recognizing an Immunodominant Peptide of Myelin Basic Protein in Multiple Sclerosis", *Journal of Immunology* 163:3530–3538 (1999).
Kosovska, M., "T cell recognition motifs of an immunodominant peptide of myelin basic protein in patients with multiple sclerosis: structural requirements and clinical implications" *Eur. J. Immunology,* 28:1894–1901 (1998).

Zang, Y.C.Q. et al. "Restricted TCR $V_\alpha$ gene rearrangements in T–Cells recognizing an immunodominant peptide of myelin basic protein in DR2 patients with multiple sclerosis" *International Immunology* 10:991–998 (1998).
Database CAPLUS, Accession No. 1998:787586, Zhang, J., "Emerging therapeutic targets in multiple sclerosis: suppression and elimination of myelin–autoreactive T–lymphocytes," abstract, *Emerging Therapeutic Targets,* 2:137–156 (1998).
Gold, D. P. et al., "Results of a phase I clinical trial of a T–cell receptor vaccine in patients with multiple sclerosis. II. Comparative analysis of TCR utilization in CSF T–cell populations before and after vaccination with a TCRVβ6 CSF T–cell populations before and after vaccination with a TCRVβ6 CDR2 peptide.", *Journal of Neuroimmunology* 76:29–38 (1997).
Goldrath, A. W. et al., "Differences in Adhesion Markers, Activation Markers, and TcR in Islet Infiltrating vs. Peripheral Lymphocytes in the NOD Mouse", *Journal of Autoimmunity* 8:209–220 (1995).
Lider, O. et al., "Anti–Idiotypic Network Induced by T Cell Vaccination Against Experimental Autoimmune Encephalomyelitis", *Science* 239:181–184 (1988).
Lund, F. E. et al., "CD38: a new paradigm in lymphocyte activation and signal transduction", *Immunological Reviews* 161:79–93 (1998).
Medaer, R. et al., "Depletion of myelin–basic–protein autoreactive T cells by T–cell vaccination; pilot trial in multiple sclerosis", *The Lancet* 346:807–8 (1995).
Sakaguchi, S. et al., "T Cell–Mediated Maintenance of Natural Self–Tolerance: its Breakdown as a Possible Cause of Various Autoimmune Diseases", *Journal of Autoimmunity* 9:211–220 (1996).

(List continued on next page.)

Primary Examiner—Ethan Whisenant
(74) *Attorney, Agent, or Firm*—Howrey Simon Arnold & White, LLP

(57) ABSTRACT

In one embodiment, the present invention is directed to a first oligonucleotide comprising the sequence of or derived from 5'-CTAGGGCGGGCGGGACTCACCTAC-3' or the nucleic acid sequence complementary thereto. The first oligonucleotide can be used with a nucleic acid of between 15 and 30 nucleotides that does not comprise the sequence of the first oligonucleotide and is found in the region from Vβ to Jβ of the Vβ13.1 gene in Vβ13.1 T cells, wherein the sequences of the oligonucleotide and the nucleic acid are not found on the same strand of the Vβ13.1 gene pair, to amplify a portion of the Vβ13.1 gene. Alternatively, the first oligonucleotide can be used with a labeling moiety in methods of detecting a LGRAGLTY motif found in T cell receptors of Vβ13.1 T cells. This motif is associated with autoimmune diseases, such as multiple sclerosis (MS). Once the motif is detected, the autoimmune disease can be treated or its progress monitored. The autoimmune disease can be treated by administering a peptide comprising the LGRAGLTY motif.

18 Claims, 5 Drawing Sheets

OTHER PUBLICATIONS

Van Gool, S. W. et al., "CD80, CD86 and CD40 Provide Accessory Signals in a Multiple–Step T–Cell Activation Model", *Immunological Reviews* 153:47–83 (1996).

Van de Stolpe, A. et al., "Intercellular adhesion molecult–1", *J. Mol. Med.* 74:13–33 (1996).

Wilson, D. B. et al., "Results of a phase I clinical trial of a T–cell receptor peptide vaccine in patients with multiple sclerosis. I. Analysis of T–cell receptor utilization in CSF cell populations", *Journal of Neuroimmunology* 76:15–28 (1997).

Zhang, J. et al., "In Vivo Clonotypic Regulation of Human Myelin Basic Protein–Reactive T Cells by T Cell Vaccination", *Journal of Immunology* 155:5868–77 (1995).

Zhang, J. et al., "MHC–Restricted Depletion of Human Myelin Basic Protein–Reactive T Cells by T Cell Vaccination", *Science* 261:1451–54 (1993).

* cited by examiner

T cell reactivity (CPM±SD)

| Alanine substituted peptides | MS1-E2.6 | MS1-C3.1 | MS1-E3.1 |
|---|---|---|---|
| 83-ENPVVHFFKNIVTPRTP-99 | 74,189 ± 6,224 | 28,966 ± 1,100 | 31,236 ± 3,099 |
| A---------------- | 59,328 ± 2,583 | 42,446 ± 676 | 38,880 ± 1,483 |
| -A--------------- | 68,881 ± 3,155 | 33,165 ± 1,883 | 31,243 ± 1,036 |
| --A-------------- | 64,901 ± 377 | 27,019 ± 3.085 | 24,487 ± 731 |
| ---A------------- | 65,519 ± 588 | 21,340 ± 1,288 | 34,289 ± 357 |
| ----A------------ | 65,205 ± 241 | 35,032 ± 5,649 | 34,080 ± 2,274 |
| -----A----------- | 74,224 ± 526 | 16,199 ± 412 | 35,242 ± 300 |
| ------A---------- | 67,916 ± 1,979 | 34,437 ± 88 | 16,853 ± 690 |
| -------A--------- | 2,504 ± 519 | 907 ± 10 | 334 ± 38 |
| --------A-------- | 51,052 ± 4,329 | 26,400 ± 3,969 | 12,577 ± 610 |
| ---------A------- | 1,787 ± 120 | 3,364 ± 275 | 1,658 ± 78 |
| ----------A------ | 69,699 ± 3,649 | 7,649 ± 337 | 16,598 ± 440 |
| -----------A----- | 1,710 ± 34 | 35,340 ± 476 | 42,982 ± 1,605 |
| ------------A---- | 48,169 ± 1,418 | 32,109 ± 570 | 21,977 ± 1,354 |
| -------------A--- | 70,946 ± 1,326 | 23,662 ± 529 | 10,237 ± 22 |
| --------------A-- | 2,389 ± 473 | 21,401 ± 432 | 2,424 ± 126 |
| ---------------A- | 1,859 ± 110 | 32,035 ± 257 | 36,930 ± 623 |
| ----------------A | 1,569 ± 32 | 31,506 ± 351 | 34,389 ± 457 |
| Medium alone | 1,763 ± 132 | 999 ± 57 | 715 ± 53 |

T-CELL RECEPTOR Vβ-Dβ-Jβ SEQUENCE AND METHODS FOR ITS DETECTION

This application claims benefit to Provisional No. 60/121,311 filed Feb. 23, 1999.

The United States government may own rights in the present invention pursuant to grant number NS36140 from the National Institutes of Health.

BACKGROUND OF THE INVENTION

1. Field of the Invention

The present invention relates generally to the field of treatment of autoimmune disease, such as multiple sclerosis (MS). More particularly, it concerns a T-cell receptor sequence found in some MS patients, and methods for its detection.

2. Description of Related Art

In humans and other mammals, T cell receptors are found on T cells. T cell receptors comprise α and β chains, with β chains comprising the following regions from N-terminus to C-terminus: Vβ-Dβ-Jβ-Cβ. T cell receptors naturally vary in the Vβ-Dβ-Jβ regions.

When an antigen is presented to the T cells by an antigen-presenting cell (APC), a T cell receptor with variable regions (including Vβ-Dβ-Jβ) that so happen to recognize the antigen binds to the antigen on the APC. The T cell bearing the T cell receptor then undergoes activation (clonal expansion).

The pathogenesis of a number of autoimmune diseases is believed to lie in autoimmune T cell responses to antigens presented normally by the organism. An example of such a disease is multiple sclerosis (MS), which is generally held to arise in T cell responses to myelin antigens, in particular myelin basic protein (MBP). MBP-reactive T cells are found to undergo in vivo activation, and occur at a higher precursor frequency in blood and cerebrospinal fluid in patients with MS as opposed to control individuals. These MBP-reactive T cells produce Th1 cytokines, e.g. IL-2, TNF, and γ-interferon. These Th1 cytokines facilitate migration of inflammatory cells into the central nervous system and exacerbate myelin-destructive inflammatory responses in MS.

A number of regulatory mechanisms can be made use of in the treatment of MS. One such is vaccination with one or more of the limited number of T cell membrane-associated peptides with extracellular domains. Vandenbark, U.S. Pat. No. 5,614,192, discloses treatment of autoimmune diseases by the use of immunogenic T cell receptor peptides of 15 to 30 amino acids comprising at least part of the second complementarity determining region (CDR2) of the T cell receptor. A copending U.S. patent application by Zhang (No. 60/099,102) discloses treatment of autoimmune diseases by use of immunogenic T cell receptor peptides in combination with immunogenic T cell activation marker peptides.

One area in which vaccination with T cell receptor peptides can be improved is by determining which, if any, common motifs are found in the T cell receptors of a patient with an autoimmune disease such as MS. If such motifs are found, then the patient can be vaccinated with peptides identical to the motifs, in order to facilitate treatment.

Therefore, it is desirable to have the amino acid sequences of common motifs found in the T cell receptors of patients with autoimmune diseases. It is also desirable to be able to readily detect such motifs in a patient sample by a convenient method, such as PCR. In addition, it is desirable to use peptides identical to the detected motifs to treat a patient with the autoimmune disease.

The present invention discloses such a common motif found in the T cell receptors of a subset of Vβ13.1 T cells, the "LGRAGLTY motif", which has the amino acid sequence Lue Gly Arg Ala Gly Leu Thr Tyr (SEQ ID NO: 3), as well as a method for its ready detection by PCR. This motif is found in some T cell receptors of some T cells that recognize amino acids 83–99 of MBP (hereinafter "MBP83–99"). The motif in the context of this subset of Vβ13.1 T cells may hereinafter be referred to as "Vβ13.1-LGRAGLTY." Peptides identical to the motif can be used to vaccinate patients in order to treat or prevent autoimmune diseases with which Vβ13.1-LGRAGLTY is associated. One such autoimmune disease is MS.

SUMMARY OF THE INVENTION

In one embodiment, the present invention is directed to an oligonucleotide from about 15 to 30 nucleotides in length which comprises at least 10 contiguous nucleotides of SEQ ID NO:1, or a sequence complementary thereto or derived therefrom. Even more preferable is an oligonucleotide, of about 15 to 30 nucleotides in length, which comprises 11, 12, 13, 14, 15, 16, 17, 18, 19, 20, 21, 22, or 23 contiguous nucleotides of SEQ ID NO:, or a sequence complementary thereto. Most preferable is an oligonucleotide, of about 15 to 30 nucleotides in length, which comprises the nucleotide sequence of SEQ ID NO:1, or the sequence complementary thereto.

In a series of further embodiments, the oligonucleotide can be used in amplification or detection of a nucleic acid sequence found in Vβ13.1-LGRAGLTY T cells. In one subseries of such embodiments, the oligonucleotide is used in a primer pair, the primer pair comprising or derived from:

(a) a first primer which is an oligonucleotide is from about 15 to 30 nucleotides in length and comprises at least 10 contiguous nucleotides of SEQ ID NO:1, or a sequence complementary thereto; and (b) a second primer which is an oligonucleotide of about 15 and 30 nucleotides in length that does not comprise the sequence (a), and said second primer sequence can be found in the region from Vβ to Jβ of the Vβ13.1 gene (SEQ ID NO: 2) in T cell receptor T cells, wherein the sequences of (a) and (b) are not found on the same strand of the T cell receptor gene.

Preferably said first primer is an oligonucleotide, of about 15 to 30 nucleotides in length, which comprises 11, 12, 13, 14, 15, 16, 17, 18, 19, 20, 21, 22, or 23 contiguous nucleotides of SEQ ID NO:1, or a sequence complementary thereto. Most preferable is an oligonucleotide, of about 15 to 30 nucleotides in length, which comprises the nucleotide sequence of SEQ ID NO:1, or the sequence complementary thereto.

In another subseries of such embodiments, the oligonucleotide is used as an oligonucleotide probe, the oligonucleotide probe comprising:

(a) an oligonucleotide from about 15 to 30 nucleotides in length and comprises at least 10 contiguous nucleotides of SEQ ID NO:1, or a sequence complementary thereto; and (b) a labeling moiety.

Preferably, the oligonucleotide, is about 15 to 30 nucleotides in length, and comprises 11, 12, 13, 14, 15, 16, 17, 18, 19, 20, 21, 22, or 23 contiguous nucleotides of SEQ ID NO:1, or a sequence complementary thereto. Most preferable is an oligonucleotide, of about 15 to 30 nucleotides in length, which comprises the nucleotide sequence of SEQ ID NO:1, or the sequence complementary thereto. The labeling moiety is preferably selected from $^{32}P$ or digoxingenin.

In another embodiment, the present invention is directed to a method of detecting MBP83–99 Vβ13.1 T cells expressing a LGRAGLTY motif, comprising:
  (i) obtaining a nucleic acid sample from MBP83–99 Vβ13.1 T cells;
  (ii) contacting the nucleic acid sample with a primer pair selected or derived from:
    (a) a first primer comprising an oligonucleotide of about 15 to 30 nucleotides in length and comprises at least 10 contiguous nucleotides of SEQ ID NO:1, or a sequence complementary thereto or derived therefrom; and
    (b) a second primer comprising and oligonucleotide of about 15 and 30 nucleotides in length that does not comprise the sequence of (a) and is found in the region from Vβ to Jβ of the Vβ13.1 gene in Vβ13.1 T cells (SEQ ID NO:2),
    wherein the sequences of (a) and (b) are not found on the same strand of the Vβ13.1 gene; and,
  (iii) detecting the presence of the nucleic acid encoding the LGRAGLTY motif.

Preferably the first primer is an oligonucleotide, of about 15 to 30 nucleotides in length, which comprises 11, 12, 13, 14, 15, 16, 17, 18, 19, 20, 21, 22, or 23 contiguous nucleotides of SEQ ID NO:, or a sequence complementary thereto. Most preferable is an oligonucleotide, of about 15 to 30 nucleotides in length, which comprises the nucleotide sequence of SEQ ID NO:1, or the sequence complementary thereto.

In yet another embodiment, the present invention is directed to a method of treating an autoimmune disease, comprising:
  (a) obtaining MBP83–99 Vβ13.1 T cells from a human;
  (b) detecting the presence of a nucleic acid encoding the LGRAGLTY motif by the method described above; and, if the nucleic acid is detected,
  (c) administering an Lue Gly Arg Ala Gly Leu Thr Tyr (SEQ ID NO: 3) peptide to the human.

In a still further embodiment, the present invention is directed to a method of monitoring an autoimmune disease, comprising:
  (a) obtaining MBP83–99 Vβ13.1 T cells from a human;
  (b) detecting the presence of a nucleic acid encoding the LGRAGLTY motif by the method described above; and, if the nucleic acid is detected,
  (c) quantifying the nucleic acid.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2 shows reactivity patterns of two MBP83–99 T cell clones to analog peptides with single alanine substitutions. Two pairs of MBP83–99 T cell clones that exhibited identical Vβ13.1 rearrangements (for MS7-E2.6 and MS27-C3.1) and a similar Vα-Jα junctional sequence (for MS7-E2.6 and MS7-E3.1) were examined for reactivity to a panel of alanine substituted peptides in [$^3$H]-thymidine incorporation assays. A mouse fibroblast cell line expressing DRB1*1501 was used as a source of antigen-presenting cells. The proliferative responses of the clones to each analog peptide were measured after 72 hours and the results are presented as CPM incorporated. The shaded boxes represent >50% decrease in the proliferation of the T cell clones in response to analog peptides.

DESCRIPTION OF PREFERRED EMBODIMENTS

Figure 1:
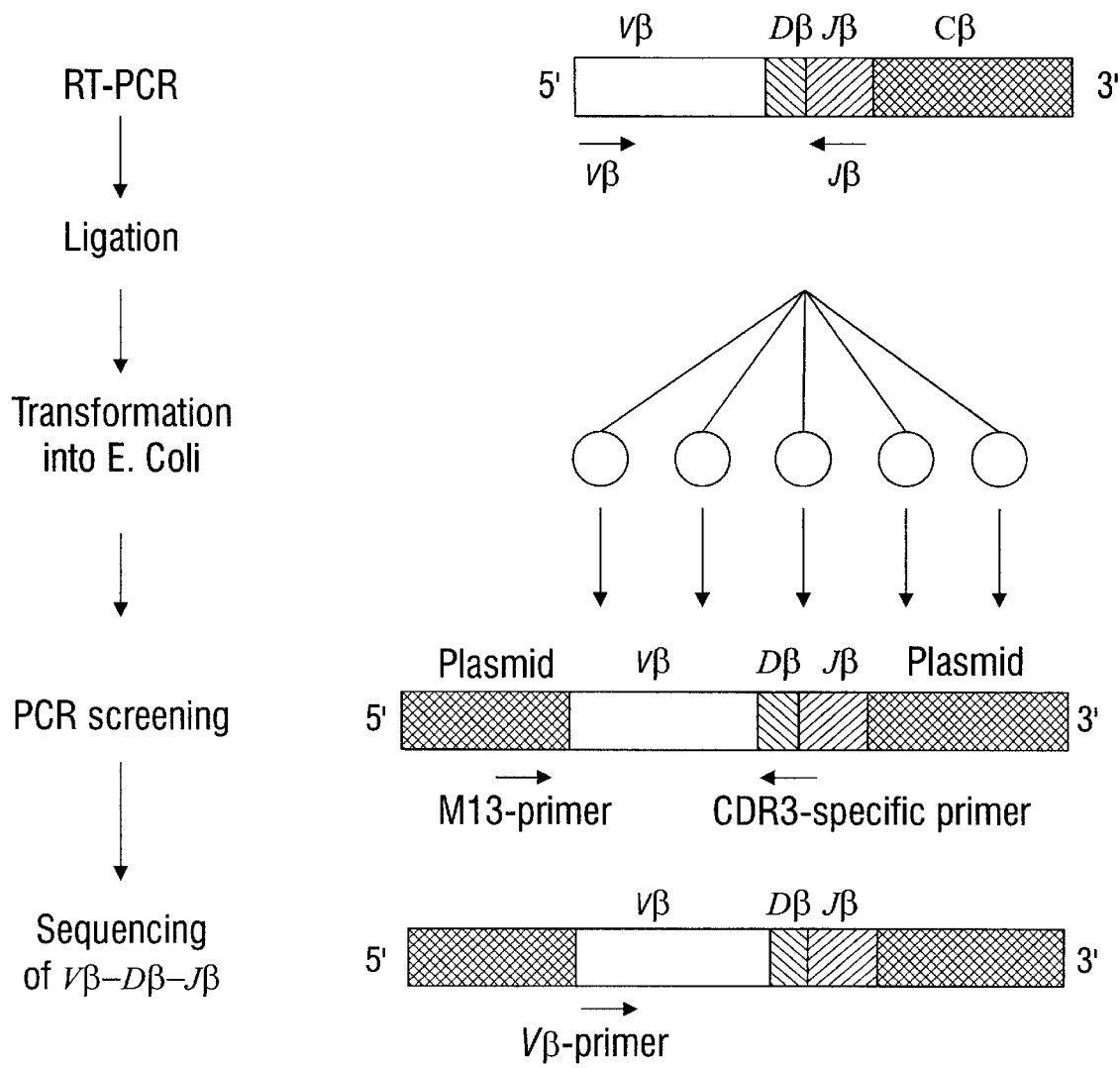
FIG. 1 shows the experimental procedure for cloning and sequencing of PBMC-derived PCR products. cDNA derived from PBMC specimens were amplified by the 5'Vβ13.1 primer and the 3'Jβ primer from four PBMC specimens positive for the expression of the LGRAGLTY motif were ligated into the TA cloning vector pCR2.1 and transformed into E. coli. Plasmid DNA was screened by PCR with a M13 primer and the LGRAGLTY-specific primer. The positive plasmids that showed visible amplification by PCR were sequenced for VβDβJβ sequences with a Vβ13.1 primer.
Figure 3:
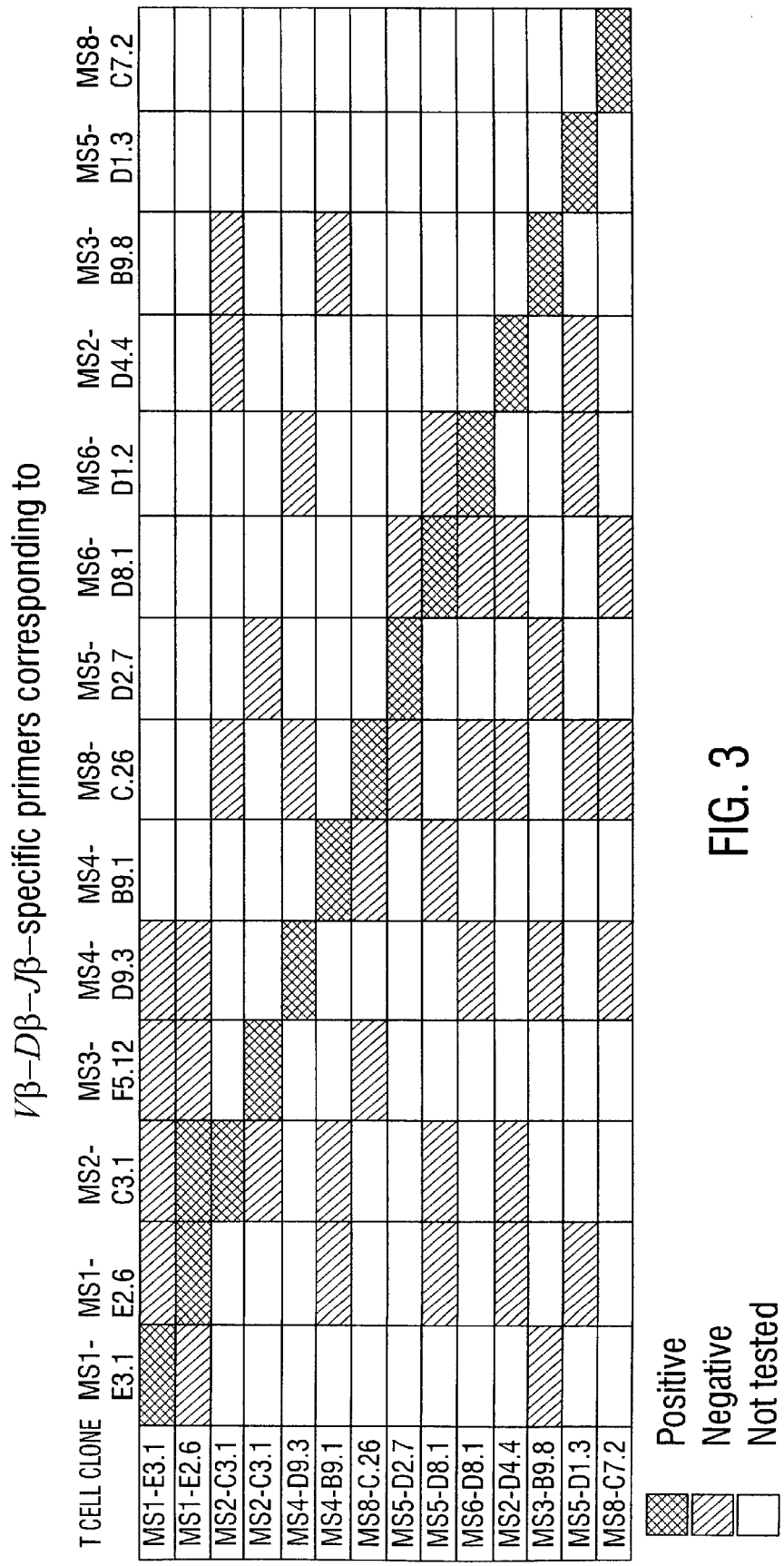
FIG. 3 shows cross-examination of the specificity of CDR3 oligonucleotides with original and unrelated T cell clones. A set of oligonucleotides specific for TCR VDJ region of were examined for their specificity in detecting known target DNA sequences present in original MBP83–99 T cell clones as well as in unrelated MBP83–99 T cell clones derived from the same and different individuals. PCR reactions using CDR3-specific oligonucleotides as the forward primers and a 3'-Cβ primer as the reverse primer performed. Solid boxes represent positive detection of DNA sequences present in original T cell clones or T cell clone(s) sharing the same CDR3 sequences. All primers were also examined for their binding to DNA products of randomly selected T cell clones that had unrelated CDR3 sequences (shaded boxes).
Figure 4:
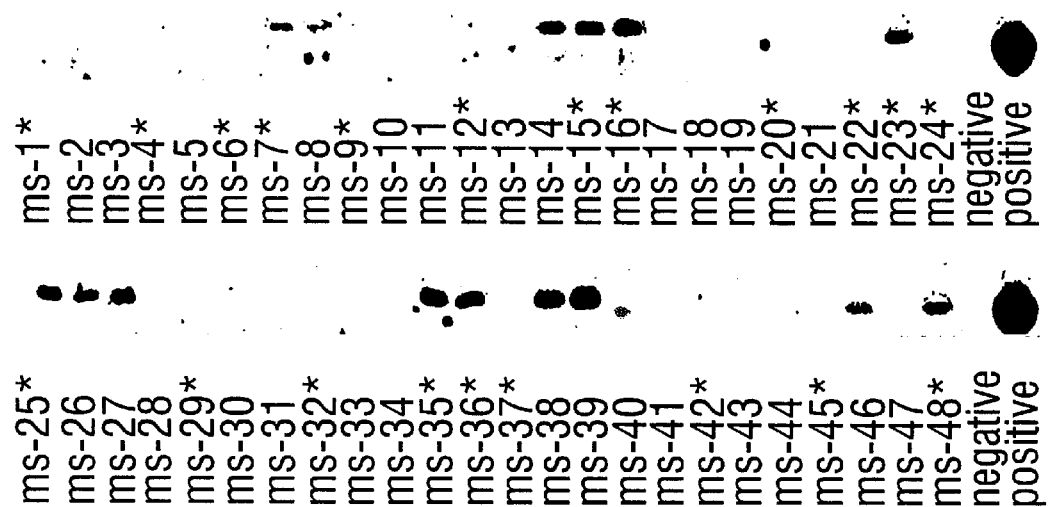
FIG. 4 shows detection of target DNA sequence complementary to motif Vβ13.1-LGRAGLTY in randomly selected PBMC specimens derived from patients with MS. cDNA prepared from PBMC specimens from randomly selected MS patients (n=48) were first amplified in RT-PCR using a 5'-Vβ13.1 specific primer and a 3'-Cβ primer. The amplified PCR products were then hybridized subsequently with a digoxigenin-labeled oligonucleotide probe specific for the LGRAGLTY motif. The original MBP83–99 clone (MS7-E2.6) and an unrelated T cell clone (MS32-B9.8) were used as positive and negative controls, respectively. MS-7 and MS-27 were the original PBMC specimens from which clone MS7-E2.6 (MS-7 in Table 1) and clone MS27-C3.1 (MS-27 in Table 1) were derived. Asterisks indicate positive expression of DRB1 *1501.
Figure 5:
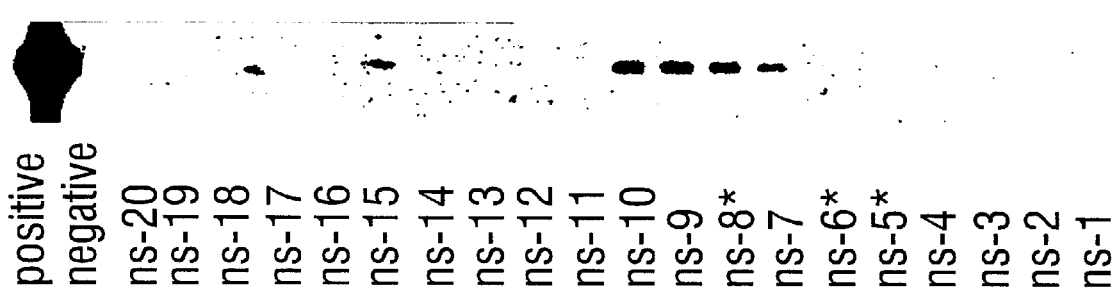
FIG. 5 shows detection of the Vβ13.1-LGRAGLTY motif in randomly selected PBMC specimens derived from normal subjects. PBMC specimens obtained from 20 normal subjects (NS) were analyzed under the same condition as described in the FIG. 4 legend. The original clone (MS7-E2.6) and an unrelated T cell clone (MS32-B9.8) were used as positive and negative controls, respectively. Asterisks indicate positive expression of DRB1*1501.
Figure 6:
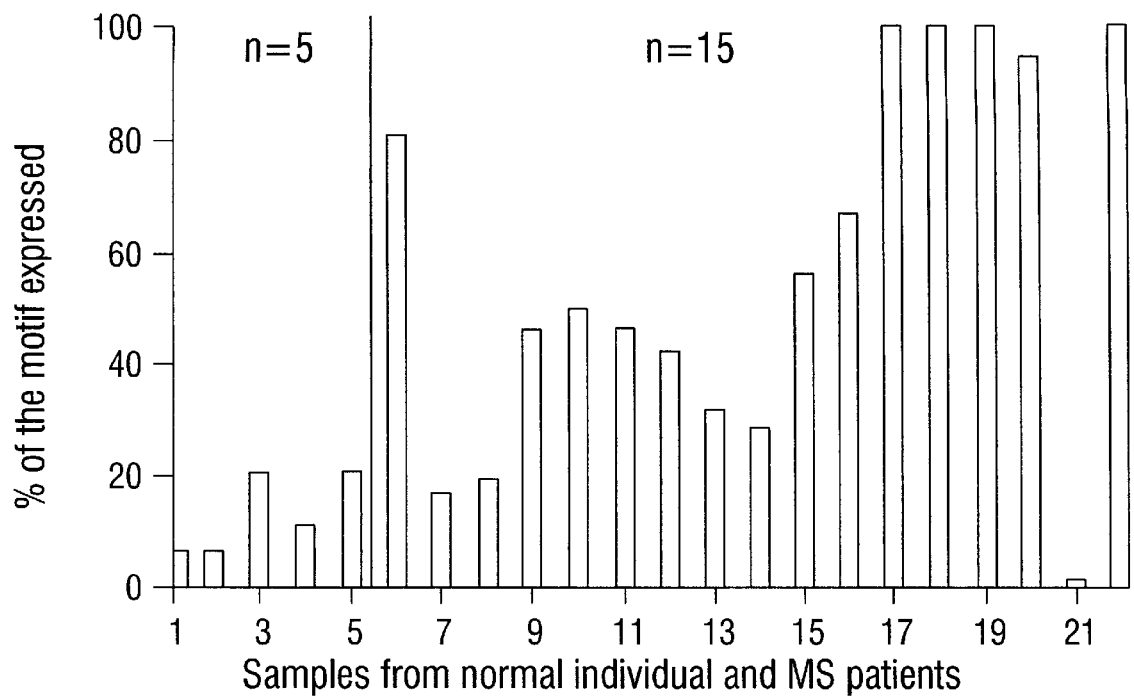
FIG. 6 shows semi-quantitative comparason of the expression of the LGRAGLTY motif in PBMC specimens derived from MS patients and normal subjects. The expression of motif Vβ13.1-LGRAGLTY was analyzed by semi-quantitative PCR relative to the Cβ expression in each cDNA derived from PBMC of MS and normal individuals. The relative expression level was calculated as (expression of the LGRAGLTY motif/Expression of Cβ)×100%.
Figure 7:
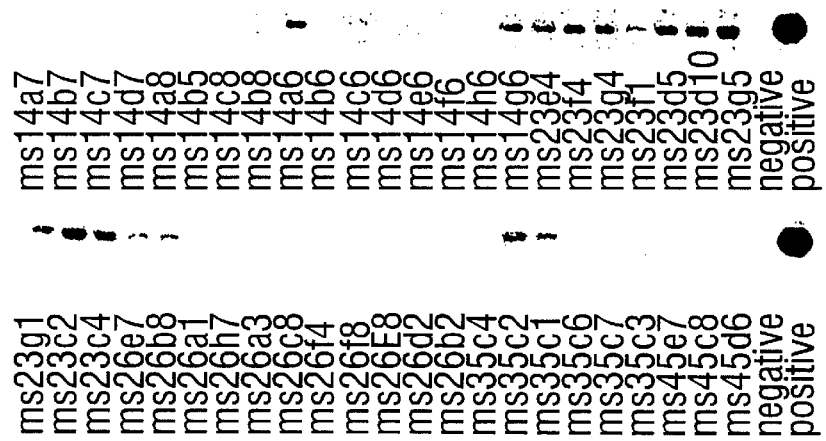
FIG. 7 shows detection of the Vβ13.1-LGRAGLTY motif in short-term MBP83–99 T cell lines derived from patients with MS. A panel of independent short-term MBP83–99 T cell lines were generated from five patients with MS using a synthetic 83–99 peptide of MBP. All these T cell lines were confirmed for their specific reactivity to MBP83–99 peptide (CPM in response to MBP83–99/control CPM>5). cDNA products were amplified using a 5'-Vβ13.1 specific primer and a 3'-Cβ primer in PCR. The amplified PCR products were hybridized subsequently with a digoxigenin-labeled oligonucleotide probe corresponding to the Vβ13.1-LGRAGLTY motif in a Southern blot analysis. cDNA products derived from the original MBP83–99 clone (MS7-E2.6) and a unrelated T cell clone (MS32-B9.8) were used as positive and negative controls, respectively.

To aid in understanding the invention, several terms are defined below.

"PCR" means the polymerase chain reaction, for example, as generally described in U.S. Pat. No. 4,683,202 (issued Jul. 28, 1987 to Mullins), which is incorporated herein by reference. PCR is an amplification technique wherein selected oligonucleotides, or primers, are hybridized to nucleic acid templates in the presence of a polymerization agent (such as polymerase) and four nucleotide triphosphates, and extension products are formed from the primers. These products are then denatured and used as templates in a cycling reaction that amplifies the number and amount of existing nucleic acids to facilitate their subsequent detection. A variety of PCR techniques are available and may be used with the methods according to the invention.

"Primer" means an oligonucleotide, whether natural or synthetic, capable of acting as a point of initiation of DNA synthesis complementary to a specific DNA sequence on a template molecule.

"Derived from," in the context of the term "primer(s) or probe(s) derived from," means that the primer or probe is not limited to the nucleotide sequence(s) listed, but also includes variations in the listed nucleotide sequence(s) including nucleotide additions, deletions, or substitutions to the extent that the variations to the listed sequence(s) retain the ability to act as a primer in the detection of T cell receptor DNA encoding the Vβ13.1-LGRAGLTY sequence, i.e. Lue Gly Arg Ala Gly Leu Thr Tyr (SEQ ID NO: 3).

"Immunogenic," when used to describe a peptide, means the peptide is able to induce an immune response, either T cell mediated, antibody, or both. "Antigenic" means the peptide can be recognized in a free form by antibodies and in the context of MHC molecules in the case of antigen-specific T cells.

"Immune-related disease" means a disease in which the immune system is involved in the pathogenesis of the disease. A subset of immune-related diseases are autoimmune diseases. Autoimmune diseases contemplated by the present invention include, but are not limited to, rheumatoid arthritis, myasthenia gravis, multiple sclerosis, systemic lupus erythematosus, autoimmune thyroiditis (Hashimoto's thyroiditis), Graves' disease, inflammatory bowel disease, autoimmune uveoretinitis, polymyositis, and certain types of diabetes. In view of the present disclosure, one skilled in the art can readily perceive other autoimmune diseases treatable by the compositions and methods of the present invention. "T cell mediated disease" means a disease brought about in an organism as a result of T cells recognizing peptides normally found in the organism.

"Treatment" or "treating," when referring to protection of an animal from a disease, means preventing, suppressing, or repressing the disease. Preventing the disease involves administering a composition of the present invention to an animal prior to induction of the disease. Suppressing the disease involves administering a composition of the present invention to an animal after induction of the disease but before its clinical appearance. Repressing the disease involves administering a composition of the present invention to an animal after clinical appearance of the disease. It will be appreciated that in human medicine it cannot always be known when in the course of disease induction a composition of the present invention will be administered.

In one aspect, the present invention is directed to a primer pair comprising the sequence of or derived from:

(a) a first primer which is an oligonucleotide of about 15 to 30 nucleotides in length, comprising at least 10 contiguous nucleotides of SEQ ID NO: 1, or the nucleic acid sequence complementary thereto; and (b) a second primer which is an oligonucleotide of about 15 and 30 nucleotides in length that does not comprise a sequence of (a) and is found in the region from Vβ to Jβ of the T cell receptor gene in Vβ13.1 T cells, wherein the sequences of (a) and (b) are not found on the same strand of the T cell receptor gene.

Preferably, said first primer is an oligonucleotide, of about 15 to 30 nucleotides in length, which comprises 11, 12, 13, 14, 15, 16, 17, 18, 19, 20, 21, 22, or 23 contiguous nucleotides of SEQ ID NO:, or a sequence complementary thereto. Most preferable is an oligonucleotide, of about 15 to 30 nucleotides in length, which comprises the nucleotide sequence of SEQ ID NO:1, or the sequence complementary thereto.

The primers according to the invention are designed to amplify a fragment of a gene encoding T cell receptor of human Vβ13.1 T cells, the fragment comprising an amino acid motif Lue Gly Arg Ala Gly Leu Thr Tyr (SEQ ID NO: 3). The gene from Vβ13.1 T cells encoding the T cell receptor comprising the LGRAGLTY motif has been submitted to GenBank, accession number AF117132. The sequence of the gene from Vβ13.1 T cells encoding the T cell receptor comprising the LGRAGLTY motif is given herein as SEQ ID NO: 2. In the method according to the invention, a fragment of about 400 bp of the T cell receptor gene from Vβ13.1 T cells is amplified using two primers, wherein the first primer is in the CDR3 region, and the second primer is in the Cβ region. The Vβ-Dβ-Jβ region of the T cell receptor gene will be between the CDR3 and Cβ regions, inclusive. In a preferred embodiment, the primers are the primer pair described above.

Primers according to the invention also include oligonucleotides that are derived from the primers (a)–(b). A sequence is derived from a primer (a) or (b) if it has or contains substantially the same sequence as one of the primers and retains the ability to selectively anneal to approximately the same CDR3 or Cβ region of the Vβ-Dβ-Jβ region of the T cell receptor gene from Vβ13.1 T cells as described above. More particularly, the primer may differ from a primer (a) or (b) in length or by the kind of nucleic acid in one or more positions along the sequence, as long as it retains selectivity for the identified regions of the Vβ-Dβ-Jβ region of the T cell receptor gene from Vβ13.1 T cells. For example, the primer may be an oligonucleotide having at least 15 nucleotides, wherein the 15 nucleotides are identical with a series of 15 contiguous nucleic acids selected or derived from a sequence of the primers (a)–(b). The primer may also be any oligonucleotide of about 30 nucleotides or less comprising a segment having the sequence selected or derived from any of primers (a)–(b). The number of nucleotides in the primer should be high enough to retain selectivity, yet low enough to retain efficiency and operability in primer synthesis and the PCR procedure. The primer may have variations including nucleotide deletions, additions, or substitutions to the extent that the variations to the sequence of primers (a)–(b) retain the ability to act as a primer in the detection of Vβ13.1 -LGRAGLTY.

The Vβ13.1-LGRAGLTY detection method according to the invention uses a pair of the above primers in a procedure that detects the presence of any Vβ13.1-LGRAGLTY in a sample. The sample to be tested for the presence of Vβ13.1-LGRAGLTY is a nucleic acid, preferably DNA. The DNA can be genomic DNA, cDNA, DNA previously amplified by PCR, or any other form of DNA. The sample can be isolated, directly or indirectly, from any animal or human bodily tissue that expresses T cell receptor β chain genes. A preferred bodily tissue is peripheral blood mononuclear cells (PBMC). If the sample is genomic DNA, it can be isolated directly from the bodily tissue. If the sample is cDNA, it is isolated indirectly by reverse transcription of mRNA directly isolated from the bodily tissue. If the sample is DNA previously amplified by PCR, it is isolated indirectly by amplification of genomic DNA, cDNA, or any other form of DNA.

In a preferred embodiment, a portion of the T cell receptor gene from Vβ13.1 T cells, the portion comprising a sequence encoding the LGRAGLTY motif, is amplified to enhance the ability to detect the presence of Vβ13.1-LGRAGLTY (5'-CTAGGGCGGGCGGGACTCACCTAC-3' (SEQ ID NO: 1)). The amplification can take place via a PCR reaction, using any particular PCR technique or equipment that provides sensitive, selective and rapid amplification of the portion in the sample.

For example, the PCR amplification can follow a procedure wherein a reaction mixture is prepared that contains the following ingredients: 5 μL 10×PCR buffer II (100 mM Tris-HCl, pH 8.3, 500 mM KCl), 3 μL 25 mM MgCl$_2$, 1 μL 10 mM dNTP mix, 0.3 μL Taq polymerase (5 U/μL) (AmpliTaq Gold, Perkin Elmer, Norwalk, Conn.), 30 pmol of primer A, and 30 pmol of primer B. In light of the present disclosure, the skilled artisan will be able to select appropriate primers A and B for the purpose of PCR amplification of the portion of the T cell receptor gene from Vβ13.1 T cells. The above mixture is appropriate for amplifying 1 μL of sample DNA. Hereinafter, the DNA to be amplified may be referred to as the "template."

Once sample DNA is added to the above reaction mixture, the PCR reaction can be performed with an amplification profile of 1 min at 95° C. (denaturation); 20 sec at 56° C. (annealing), and 40 sec at 72° C. (extension) for a total of 35 cycles.

In the PCR reaction, the template can be heat denatured and annealed to two oligonucleotide primers. The oligonucleotides bracket an area of the nucleic acid sequence that is to be amplified. A heat stable DNA polymerase is included in the reaction mixture. The polymerase elongates the primers annealed to complementary DNA by adding the appropriate complementary nucleotides. Preferred polymerases have the characteristics of being stable at temperatures of at least 95° C., have a processivity of 50–60 and have an extension rate of greater than 50 nucleotides per minute.

Approximately 40 PCR cycles are used in a typical PCR amplification reaction. However, certain PCR reactions may work with as few as 15 to 20 cycles or as many as 50 cycles. Each cycle consists of a melting step in which the template is heated to a temperature above about 95° C.

The temperature of the PCR reaction is then cooled to allow annealing of the primers to the template. In this annealing step, the reaction temperature is adjusted to between about 55° C. to 72° C. for approximately 20 seconds. Longer or shorter times may work depending upon the specific reaction.

The temperature of the PCR reaction is then heated to allow maximal elongation of the primers to be effected by the polymerase. In this extension step, the reaction temperature is adjusted to between about 70° C. and 75° C. for approximately 40 seconds. Higher or lower temperatures and/or longer or shorter times may work depending upon the specific reaction.

In addition, before the first cycle is begun, the reaction mixture can undergo an initial denaturation for a period of about 5 min to 15 min. Similarly, after the final cycle is ended, the reaction mixture can undergo a final extension for a period of about 5 min to 10 min.

Amplification can be performed using a two-step PCR. In this technique, a first PCR amplification reaction is performed to amplify a first region that is larger than, and comprises, a region of interest. A second PCR amplification reaction is then performed, using the first region as a template, to amplify the region of interest. If either primer from the first PCR reaction can be used in the second PCR reaction, the second PCR reaction is "semi-nested." If neither primer from the first PCR reaction can be used in the second PCR reaction, the second PCR reaction is "nested."

In a preferred way of performing the method of the present invention, the Vβ13.1 -LGRAGLTY motif is amplified by two-step PCR. In the first PCR reaction, the sample is amplified using a first primer that anneals to the Vβ region of the T cell receptor gene and a second primer that anneals to the Cβ region of the T cell receptor gene, using the reaction mixture and profile disclosed above. The first PCR reaction amplifies a first region that is about 600 bp and extends from Vβ through the Vβ-Dβ-Jβ junction to Cβ. The second PCR reaction is nested or semi-nested; a portion of the first region is partially amplified using primer pair (a)–(b). The second PCR reaction amplifies the region of interest.

After amplification of any DNA encoding Vβ13.1-LGRAGLTY in the sample, the amplification product is detected. This detection may be done by a number of procedures. For example, an aliquot of amplification product can be loaded onto an electrophoresis gel, to which an electric field is applied to separate DNA molecules by size. In another method, an aliquot of amplification product is loaded onto a gel stained with SYBR green, ethidium bromide, or another molecule that will bind to DNA and emit a detectable signal. For example, ethidium bromide binds to DNA and emits visible light when illuminated by ultraviolet light. A dried gel could alternatively contain a radio- or chemically-labeled oligonucleotide (which may hereinafter be termed an "oligonucleotide probe") complementary to a portion of the sequence of the amplified template, from which an autoradiograph is taken by exposing the gel to film.

In another embodiment, the present invention relates to an oligonucleotide probe, comprising (a) a oligonucleotide of about 15 to 30 nucleotides in length, comprising at least 10 contiguous nucleotides of SEQ ID NO:1, or the nucleic acid sequence complementary thereto; and (b) a labeling moiety.

Preferably "(a)" is an oligonucleotide, of about 15 to 30 nucleotides in length, which comprises 11, 12, 13, 14, 15, 16, 17, 18, 19, 20, 21, 22, or 23 contiguous nucleotides of SEQ ID NO:1, or a sequence complementary thereto. Most preferable is an oligonucleotide, of about 15 to 30 nucleotides in length, which comprises the nucleotide sequence of SEQ ID NO:1, or the sequence complementary thereto. Preferably, the labeling moiety is selected from $^{32}$P or digoxingenin.

A typical radiolabeled oligonucleotide useful for detection of amplification products produced using primers of the present invention is taken from the Vβ-Dβ-Jβ region. If the Vβ13.1-LGRAGLTY region is amplified by the two-step semi-nested PCR disclosed above, wherein a primer corresponding to the sequence encoding the LGRAGLTY motif is used, any oligonucleotide of about 10 or more nucleotides, and preferably about 18 or more nucleotides, that is complementary to a portion of either strand of the amplified Vβ13.1-LGRAGLTY region can be used. More preferably, the oligonucleotide 5'-CTAGGGCGGGCGGGACTCACCTAC-3' (SEQ ID NO: 1) or the nucleic acid sequence complementary thereto is used as a probe.

The present invention also comprises a test kit, comprising at a first primer (a) of about 15 to 30 nucleotides in length comprising at least 10 contiguous nucleotides of SEQ ID NO: 1, or an the nucleic acid sequence complementary thereto.

In one preferred embodiment, the test kit further comprises a second primer (b), wherein the second primer is a nucleic acid sequence of about 15 and 30 nucleotides in length that does not comprise the sequence of (a) and is found in the region from Vβ to Jβ of the Vβ13.1 T cell receptor gene in T cells, wherein the sequences of (a) and (b) are not found on the same strand of the T cell receptor gene.

More preferably said first primer is an oligonucleotide, of about 15 to 30 nucleotides in length, which comprises 11, 12, 13, 14, 15, 16, 17, 18, 19, 20, 21, 22, or 23 contiguous nucleotides of SEQ ID NO:1, or a sequence complementary thereto. Most preferable is an oligonucleotide, of about 15 to 30 nucleotides in length, which comprises the nucleotide sequence of SEQ ID NO:1, or the sequence complementary thereto In this embodiment, the test kit further comprises at least one reagent useful in the amplification of Vβ13.1-LGRAGLTY DNA by PCR techniques as described above. Exemplary reagents that can be included in the kit include, but are not limited to, buffers, deoxynucleoside triphosphates, heat-stable DNA polymerase such as Taq polymerase, Vβ13.1-LGRAGLTY DNA for positive control, and non-Vβ13.1-LGRAGLTY DNA for negative control. Other reagents that can be included in the test kit are known to one skilled in the art.

In another preferred embodiment, the test kit further comprises a labeling moiety. Preferably the labeling moiety is $^{32}$P or digoxingenin.

The present invention also comprises a method of treating an autoimmune disease. The disease is one in which, for at least some patients, T cell receptors comprising LGRAGLTY are found on Vβ13.1 T cells. Other types of T cells, and/or Vβ3.1 T cells which lack T cell receptors comprising the LGRAGLTY motif, may be presented by the patient.

The method of treating the autoimmune disease comprises:
(a) obtaining MBP83–99 Vβ13.1 T cells from a human;
(b) detecting in the T cells the presence of a nucleic acid encoding a LGRAGLTY motif by the methods disclosed above; and, if the nucleic acid is detected,
(c) administering an Lue Gly Arg Ala Gly Leu Thr Tyr (SEQ ID NO: 3) peptide to the human.

The autoimmune disease can be any autoimmune disease in which T cell receptors comprising the LGRAGLTY motif are found on Vβ13.1 T cells. Autoimmune diseases contemplated by the present invention include, but are not limited to, rheumatoid arthritis, myasthenia gravis, multiple sclerosis, systemic lupus erythematosus, autoimmune thyroiditis (Hashimoto's thyroiditis), Graves' disease, inflammatory bowel disease, autoimmune uveoretinitis, polymyositis, and certain types of diabetes. A preferred autoimmune disease is multiple sclerosis (MS).

If nucleic acid encoding an LGRAGLTY motif is detected by the methods disclosed above, the autoimmune disease can be treated by administering a peptide comprising Lue Gly Arg Ala Gly Leu Thr Tyr (SEQ ID NO: 3). The peptide can be administered alone, or in combination with a T cell activation marker peptide. Preferably the peptide is administered in combination with a T cell activation marker peptide, according to the disclosure of Zhang, U.S. patent application Ser. No. 60/099,102, incorporated herein by reference. Administration of the peptide can lead to an immunogenic response, wherein the patient will develop antibodies and T cell receptors that recognize and bind to the LGRAGLTY motif of T cell receptors found on Vβ13.1 T cells.

Because Vβ13.1-LGRAGLTY can be present in both patients suffering from MS and normal individuals who are not suffering from the disease, it is envisioned that an Lue Gly Arg Ala Gly Leu Thr Tyr (SEQ ID NO: 3) peptide can be administered to both patients with MS and normal individuals.

In an alternative embodiment, if nucleic acid encoding an LGRAGLTY motif is detected by the methods disclosed above, the autoimmune disease can be monitored by quantifying the nucleic acid. The greater the amount of the nucleic acid present in a sample, such as PBMC, the greater the number of Vβ13.1 T cells and the greater the likely severity of symptoms of the autoimmune disease. Also, depending on the time between the presentation of elevated Vβ13.1 T cell levels and the appearance of symptoms, the clinician may receive an opportunity to apply treatments intended to minimize the severity of the symptoms and/or treat the disease before the symptoms appear.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

T cell receptor Vβ-Dβ-Jβ DNA sequence and sequence motifs shared among MBP83–99 specific T cell clones derived from different patients with MS A panel of 20 CD4+ independent T cell clones was generated from seven patients with MS. All T cell clones recognized the 83–99 peptide of myelin basic protein (MBP83–99) in the context of HLA-DR2 as determined by using mouse fibroblast cells (L cells) transfected with DRB1*1501 as antigen-presenting cells. The T cell clones were characterized for TCR V gene rearrangements in reverse-transcript PCR (RT-PCR) using Vα- and Vα-specific oligonucleotide primers and subsequently sequenced for the Vα-Jα and Vβ-Dβ-Jβ junctional regions. The sequences of the junctional regions are shown in Tables 1 and 2.

Table 1. summarizes the results of analysis with a panel of 20 independent MBP83–99 specific T cell clones characterized according to their Vα gene usage by reverse-transcript PCR using a panel of oligonucleotide primers specific for Vα gene families (the sequence of the unique primers used are indicated by being underlined in the DNA sequence corresponding to each clone). The amino acid sequences of the "Vα", "n", "Jα", and "Cα" portions of each clone are indicated in Table 1. as follows: the "n" portions are underlined, the "Vα" and "Jα" sequences are shown in bold on their respective sides of the "n" sequence, and the "Cα" sequence is shown in normal font without being underlined. The amplified PCR products were hybridized with digoxingenin-labeled Cα cDNA probes and were analyzed subsequently for DNA sequence.

Table 2. summarizes the results of an analysis of a panel of 20 independent MBP83–99 specific T cell clones. The clones were analyzed for Vβ gene usage by reverse-transcript PCR using a set of oligonucleotide primers specific for twenty-six Vβ gene families (sequence of the specific primer for each clone is indicated by being underlined in the corresponding DNA sequence). The "Vβ", "D", "Jβ", and "Cβ" portions of each clone are indicated in Table 2. as follows: the "D" portions are underlined, the "Vβ" and "Jβ" sequences are shown in boldface type on their respective sides of the "D" sequence, and the remaining sequence, "Cβ", is in normal font (not underlined or emboldened). The amplified PCR products were hybridized with digoxingenin-labeled Cβ cDNA probes and were analyzed subsequently for DNA sequence.

TABLE 1

TCR Vα gene sequence specific for MBP83-99 peptide

| T CELL CLONE (GenBank Accession #) | Vgene | DNA or Amino Acid | Sequence Vα-n-Jα-Cα |
|---|---|---|---|
| M57-E3.1 (AF117142) | Vα22 | Amino Acid DNA | YFCALSRGGSNYKLTFGKGTLLTVNPNIQN (SEQ ID NO:4) TACTTCTGTGCTCTGAGTAGGGGAGGTAGCAACTATA AACTGACATTTGGAAAAGGAACTCTCTTAACCGTGAA TCCAAATATCCAGAAC (SEQ ID NO:5) |
| M57-D2.2 (AF117143) | Vα9 | Amino Acid DNA | YYCALKRNFGNEKLTFGTGTRLTIIPMQN (SEQ ID NO:6) TATTACTGTGCTCTAAAAAGAAACTTTGGAAATGAGAAAT TAACCTTTGGGACTGGAACAAGACTCACCATCATACCCAA TATCCAGAAC (SEQ ID NO:7) |
| MS7-E2.6 (AF117144) | Vα17 | Amino Acid DNA | YFCAASPGGSNYKLTFGKGTLLTVNPNIQN (SEQ ID NO:8) TACTTCTGTGCAGCAAGCCCCGGAGGTAGCAACTATAAAC TGACATTTGGAAAAGGAACTCTCTTAACCGTGAATCCAAA TATCCAGAAC (SEQ ID NO:9) |
| M57-C3.1 (AF117145) | Vα17 | Amino Acid DNA | YFCAAMGDFGNEKLTFGTGTRLTIIPNIQN (SEQ ID NO:10) TACTTCTGTGCAGCAATGGGGGACTTTGGAAATGAGAAAT TAACCTTTGGGACTGGAACAAGACTCACCATCATACCCAA TATCCAGAAC (SEQ ID NO:11) |
| MS27-D7.16 (AF117145) | Vα17 | Amino Acid DNA | YFCAAMGDFGNEKLTFGTGTRLTIIPNIQN (SEQ ID NO:12) TACTTCTGTGCAGCAATGGGGGACTTTGGAAATGAGAAAT TAACCTTTGGGACTGGAACAAGACTCACCATCATACCCAA TATCCAGAAC (SEQ ID NO:13) |
| M527-F3.4 (AFIT7T45) | Vα17 | Amino Acid DNA | YFCAAMGDFGNEKLTFGTGTRLTIIPNIQN (SEQ ID NO:14) TACTTCTGTGCAGCAATGGGGGACTTTGGAAATGAGAAAT TAACCTTTGGGACTGGAACAAGACTCACCATCATACCCAA TATCCAGAAC (SEQ ID NO:15) |
| M527-D4.4 (AF117146) | Vα22 | Amino Acid DNA | YFCALSVAGGTSYGKLTFGQGTILTVHPNIQN (SEQ ID NO:16) TACTTCTGTGCTCTGAGCGTTGCTGGTGGTACTAGCTATGG AAAGCTGACATTTGGACAAGGGACCATCTTGACTGTCCAT CCAAATATCCAGAAC (SEQ ID NO:17) |
| MS32-F5.12 (AF117147) | Vα16 | Amino Acid DNA | YYCLVGDAVRPGGGNKLTFGTGTQLKVELNIQN (SEQ ID NO:18) TACTACTGCCTCGTGGGTGACGCCGTGAGGCCGGGAGGA GGAAACAAACTCACCTTTGGGACAGGCACTCAGCTAAAA GTGGAACTCAATATCCAGAAC (SEQ ID NO: 19) |
| M532-B9.8 (AF117147) | Vα16 | Amino Acid DNA | YYCLVGDAVRPGGGNKLTFGTGTQLKVELNIQN (SEQ ID NO:20) TACTACTGCCTCGTGGGTGACGCCGTGAGGCCGGGAGGA GGAAACAAACTCACCTTTGGGACAGGCACTCAGCTAAAA GTGGAACTCAATATCCAGAAC (SEQ ID NO:21) |
| MS37-D9.3 | Vα3 | Amino Acid | YFCATDAGGTYKYIFGTGTRLKVLANIQN (SEQIDNO:22) TACTTCTGTGCTACGGACGCAGGAGGAACCTACAAATACA |

TABLE 1-continued

TCR Vα gene sequence specific for MBP83-99 peptide

| T CELL CLONE (GenBank Accession #) | Vgene | DNA or Amino Acid | Sequence Vα-n-Jα-Cα |
|---|---|---|---|
| (AF117148) | | DNA | TCTTTGGAACAGGCACCAGGCTGAAGGTTTTAGCAAATAT CCAGAAC (SEQ ID NO:23) |
| MS37-B9.1 (AF117149) | Vα16 | Amino Acid | YYCLVGDIDDMRFGAGTRLTVKPNIQN (SBQIDNO: 24) |
| | | DNA | TACTACTGCCTCGTGGGTGACATCGATGACATGCGCTTTG GAGCAGGGACCAGACTGACAGTAAAACCAAATATCCAGA AC (SEQ ID NO:25) |
| MS9-C.26 (AF117150) | Vα3 | Amino Acid | YFCATSVNTDKLIFGTGTRLQVFPNIQN** (SEQ ID NO: 26) |
| | | DNA | TACTTCTGTGCTACATCGGTTAACACCGACAAGCTCATCTT TGGGACTGGGACCAGATTACAAGTCTTTCCAAATATCCAG AAC (SEQ ID NO:27) |

TABLE 2

TCR Vβ gene sequence specific for MBP83-99 peptide

| T CELL CLONE (GenBank Accession #) | Vgene | DNA or Amino Acid | Sequence Vβ-n-Jβ-Cβ |
|---|---|---|---|
| MS7-E3.1 (AF117130) | Vβ9 | Amino Acid | YFCASSQDRFWGGTVNTEAFFGQGTRLTVVEDLNK (SEQ ID NO:28) |
| | | DNA | TATTTCTGTGCCAGCAGCCAAGATCGTTTTTGGGGGGG GACGGTGAACACTGAAGCTTTCTTTGGACAAGGCACC AGACTCACAGTTGTAGAGGACCTGAACAAG (SEQ ID NO: 29) |
| M57-D2.2 (AF117131) | Vβ1 | Amino Acid | YFCASSAMGETQYFGPGTRLLVI**LEDLKN (SEQ ID NO:30) |
| | | DNA | TATTTCTGTGCCAGCAGCGCTATGGGAGAGACCCAGT ACTTCGGGCCAGGCACGCGGCTCCTGGTGCTCGAGGA CCTGAAAAAC (SEQ ID NO:31) |
| MS7-E2.6 (AF117132) | Vβ13 | Amino Acid | YFCASSLGRAGLTYEQYFGPGTRLTVTEDLKN (SEQ ID NO:32) |
| | | DNA | TACTTCTGTGCCAGCAGCCTAGGGCGGGCGGGACTCA CCTACGAGCAGTACTTCGGGCCGGGCACCAGGCTCAC GGTCACAGAGGACCTGAAAAAC (SEQ ID NO:33) |
| MS27-C3.1 (AF117132) | Vβ13.1 | Amino Acid | YFCASSLGRAGLTYEQYFGPGTRLTVTEDLKN (SEQ ID NO:34) |
| | | DNA | TACTTCTGTGCCAGCAGCCTAGGGCGGGCGGGACTCA CCTACGAGCAGTACTTCGGGCCGGGCACCAGGCTCAC GGTCACAGAGGACCTGAAAAAC (SEQ ID NO:35) |
| MS27-D7.16 (AF117132) | Vβ13.1Y | Amino Acid | YCASSLGRAGLTYEQYFGPGTRLTVTEDLKN (SEQ ID NO:36) |
| | | DNA | TACTTCTGTGCCAGCAGCCTAGGGCGGGCGGGACTCA CCTACGAGCAGTACTTCGGGCCGGGCACCAGGCTCAC GGTCACAGAGGACCTGAAAAAC (SEQ ID NO:37) |
| MS27-F3.4 (AF117132) | Vβ13.1 | Amino Acid | YFCASSLGRAGLTYEQYFGPGTRLTVTEDLKN (SEQ ID NO:38) |
| | | DNA | TACTTCTGTGCCAGCAGCCTAGGGCGGGCGGGACTCA CCTACGAGCAGTACTTCGGGCCGGGCACCAGGCTCAC GGTCACAGAGGACCTGAAAAAC (SEQ ID NO:39) |
| M527-D4.4 (AF117133) | Vβ9 | Amino Acid | YFCASSPTVNYGYTFGSGTRLTVVEDLNK (SEQ ID NO:40) |
| | | DNA | TATTTCTGTGCCAGCAGCCCGACAGTTAACTATGGCTA CACCTTCGGTTCGGGGACCAGGTTAACCGTTGTAGAG GACCTGAACAAG (SEQ ID NO:41) |
| MS32-F5.12 (AF117134) | Vβ13.1 | Amino Acid | YFCASSYSJRGQGNEQYFGPGTRLTVTEDLKN (SEQ ID NO:42) |
| | | DNA | TACTTCTGTGCCAGCAGTTACTCGATTAGGGGACAGG GTAACGAGCAGTACTTCGGGCCGGGCACCAGGCTCAC GGTCACAGAGGACCTGAAAAAC (SEQ ID NO:43) |
| M53 2-B9.8 (AF117134) | Vβ13.1 | Amino Acid | YFCASSYSIRGQGNEQYFRPGTRLTVTEDLKN (SEQ ID NO:44) |
| | | DNA | TACTTCTGTGCCAGCAGTTACTCGATTAGGGGACAGG GTAACGAGCAGTACTTCCGGCCGGGCACCAGGCTCAC GGTCACAGAGGACCTGAAAAAC (SEQ ID NO:45) |

| Clone | Vβ | Type | Sequence |
|---|---|---|---|
| MS37-D9.3 (AF119246) | Vβ7 | Amino Acid | YLCASSQDRVAPQYFGPGTRLLVLEDLKN (SEQ ID NO:46) |
| | | DNA | TATCTCTGTGCCAGCAGCCAAGATCGGGTTGCGCCACAGTACTTCGGGCCAGGCACGCGGCTCCTGGTGCTCGAGGACCTGAAAAAC (SEQ ID NO:47) |
| MS37-B9.1 (AF117135) | Vβ17 | Amino Acid | YLCASSTRQGPQETQYFGPGTRLLVLEDLKN (SEQ ID NO:48) |
| | | DNA | TATCTCTGTGCCAGTAGTACCCGGCAAGGACCTCAAGAGACCCAGTACTTCGGGCCAGGCACGCGGCTCCTGGTGCTCGAGGACCTGAAAAAC (SEQ ID NO:49) |
| MS8-D2.7 (AF117136) | Vβ8 | Amino Acid | YLCASSLGQGAYEQYFGPGTRLTVTEDLKN (SEQ ID NO:50) |
| | | DNA | TATCTCTGTGCCAGCAGCTTAGGACAGGGGGCTTACGAGCAGTACTTCGGGCCGGGCACCAGGCTCACGGTCACAGAGGACCTGAAAAAC (SEQ ID NO:51) |
| MS8-A2.7 (AF117136) | Vβ8 | Amino Acid | YLCASSLGQGAYEQYFGPGTRLTVTEDLKN (SEQ ID NO:52) |
| | | DNA | TATCTCTGTGCCAGCAGCTTAGGACAGGGGGCTTACGAGCAGTACTTCGGGCCGGGCACCAGGCTCACGGTCACAGAGGACCTGAAAAAC (SEQ ID NO:53) |
| MS8-A1.15 (AF117136) | Vβ8 | Amino Acid | YLCASSLGQGAYEQYFGPGTRLTVTEDLKN (SEQ ID NO:54) |
| | | DNA | TATCTCTGTGCCAGCAGCTTAGGACAGGGGGCTTACGAGCAGTACTTCGGGCCGGGCACCAGGCTCACGGTCACAGAGGACCTGAAAAAC (SEQ ID NO:55) |
| MS8-D1.3. (AF117137) | Vβ8 | Amino Acid | YFCASSLQVYSPLHFGNGTRLTVTEDLNK (SEQ ID NO:56) |
| | | DNA | TACTTCTGTGCCAGCAGTTTACAAGTGTATTCACCCCTCCACTTTGGGAACGGGACCAGGCTCACTGTGACAGAGGACCTGAACAAG (SEQ ID NO:57) |
| MS33-D1.2 (AF117138) | Vβ12 | Amino Acid | YFCAISESIGTGTEAFFGQGTRLTVVEDLNK (SEQ ID NO:58) |
| | | DNA | TACTTCTGTGCCATCAGTGAGTCGATTGGTACGGGAACTGAAGCTTTCTTTGGACAAGGCACCAGACTCACAGTTGTAGAGGACCTGAACAAG (SEQ ID NO:59) |
| MS33-D3.3 (AF117138) | Vβ12 | Amino Acid | YFCAISESTGTGTEAFFGQGTRLTVVEDLNK (SEQ ID NO:60) |
| | | DNA | TACTTCTGTGCCATCAGTGAGTCGATTGGTACGGGAACTGAAGCTTTCTTTGGACAAGGCACCAGACTCACAGTTGTAGAGGACCTGAACAAG (SEQ ID NO: 61) |
| MS33-D8.1 (AF117139) | Vβ3 | Amino Acid | YLCASRDRSYEQYFGPGTRLTVTEDLKN (SEQ ID NO:62) |
| | | DNA | TACCTCTGTGCCAGCCGGGACAGGTCCTACGAGCAGTACTTCGGGCCGGGCACCAGGCTCACGGTCACAGAGGACCTGAAAAAC (SEQ ID NO: 63) |
| MS9-C.26 (AF117140) | Vβ12 | Amino Acid | YFCAISEGSSSGNTIYFGEGSWLTVVEDLNK (SEQ ID NO:64) |
| | | DNA | TACTTCTGTGCCATCAGTGAGGGGTCCAGCTCTGGAAACACCATATATTTTGGAGAGGGAAGTTGGCTCACTGTTGTAGAGGACCTGAACAAG (SEQ ID NO:65) |
| MS35-C7.2 (AF117141) | Vβ2 | Amino Acid | FYICSAIDGYTFGSGTRLTVVEDLNK (SEQ ID NO:66) |
| | | DNA | TTCTACATCTGCAGTGCTATAGACGGCTACACCTTCGGTTCGGGGACCAGGTTAACCGTTGTAGAGGACCTGAACAAG (SEQ ID NO:67) |

Although the Vα and Vβ rearrangements varied between individual MBP83–99 T cell clones, many of these independent T cell clones derived from a given individual shared identical Vα and Vβ chains with the same Vα-Jα and Vβ-Dβ-Jβ junctional region sequences. The finding is consistent with in vivo clonal expansion of MBP83–99 specific T cells in given patients with MS as reported previously (Vandevyver 1995, Wucherpfennig 1994).

Interestingly, as indicated in Tables 1 and 2, an independent T cell clone (clone E2.6) derived from one patient (MS-1) shared the same Vβ13.1 and Vα17 with 3 of 4 T cell clones (clones C3.1, D7.16 and F3.4) obtained from another patient (MS-2). Vβ13.1 of these T cell clones shared an identical DNA sequence within the Vβ-Dβ-Jβ junctional region.

Example 2

Vβ-Dβ-Jβ-specific oligonucleotide primers were highly specific and sensitive in detecting corresponding DNA sequences present in original MBP83–99 T cell clones as well as in PBMC containing original MBP83–99 T cells A set of 14 oligonucleotide primers were synthesized according to DNA sequences within the Vβ-Dβ-Jβ junctional regions of independent MBP83–99 T cell clones and subsequently examined for their specificity in RT-PCR. The DNA sequences of these oligonucleotide primers are shown in Table 3.

TABLE 3

DNA sequences of Vβ-Dβ-Jβ-specific oligonucleotide primers

| T cell clone | DNA sequence | SEQ ID NO |
|---|---|---|
| MS1-E3.1 | AGCAGCCAAGATCGTTTTTGG | SEQ ID NO:68 |
| MS1-B2.6 | CTAGGGCGGGCGGGACTCACCTAC | SEQ ID NO:69 |

TABLE 3-continued

DNA sequences of Vβ-Dβ-Jβ-specific oligonucleotide primers

| T cell clone | DNA sequence | SEQ ID NO |
|---|---|---|
| MS2-C3.1 | CTAGGGCGGGCGGGACTCACCTAC | SEQ ID NO:70 |
| MS2-D4.4 | | |
| MS3-F5.12 | TACTCGATTAGGGGACAGGGTAAC | SEQ ID NO:71 |
| MS3LB9.8 | | |
| MS4-D9.3 | CAAGATCGGGTTGCGCCA | SEQ ID NO:72 |
| MS4-B9.1 | ACCCGGCAAGGACCTCAAGAGACC | SEQ ID NO:73 |
| MS5-D2.7 | AGCTTAGGACAGGGGGCT | SEQ ID NO:74 |
| MS5-D1.3 | | |
| MS6-D8.1 | GCCAGCCGGGACAGGTCC | SEQ ID NO:75 |
| MS6-D1.2 | GAGTAGATTGGTACGGGA | SEQ ID NO:76 |
| MS7-C.26 | | |
| MS8-C7.2 | TACATCTGAAGTGCTATAGAC | SEQ ID NO:77 |

These Vβ-Dβ-Jβ-specific primers bound exclusively to DNA sequences present in the original MBP83–99 T cell clones and did not bind to the sequences derived from unrelated MBP83–99 T cell clones (FIG. 2), suggesting their high specificity for the original Vβ-Dβ-Jβ DNA sequences. The only exception was noted for clone MS1-E2.6 and clone MS2-C3.1, in which the same primer bound to a Vβ-Dβ-Jβ junctional DNA sequence shared by both T cell clones.

Given the specificity of the Vβ-Dβ-Jβ oligonucleotide primers and high sensitivity of PCR detection system, we asked whether this two-step PCR detection system using 5' Vβ primers and Vβ-DβJβ-specific oligonucleotide primers could be used to detect corresponding Vβ-Dβ-Jβ DNA sequences present in peripheral blood mononuclear cells (PBMC) specimens from which the MBP83–99 T cell clones originated. The results of two separate experiments showed positive detection of the Vβ-Dβ-Jβ sequences in original PBMC specimens. Thus, the findings demonstrated that the PCR detection system where Vβ-Dβ-Jβ sequence served as a fingerprint was specific and sensitive in tracing MBP83–99 T cells present in peripheral blood mononuclear cells by probing identical DNA sequences.

Example 3

The Detection of a Common Vβ-Dβ-Jβ DNA Sequence in PBMC Specimens Derived from Different Patients with MS and Healthy Individuals Next, we examined whether DNA sequences corresponding to Vβ-Dβ-Jβ junctional regions of the MBP83–99 T cell clones could be detected in PBMC specimens randomly selected from a group of patients with MS and healthy individuals. The same PCR amplification system using primers specific for corresponding Vβ families (in the first PCR) and primers specific for Vβ-Dβ-Jβ sequences (in the second semi-nested PCR) was employed. It was combined with Southern blot analysis with corresponding Vβ-Dβ-Jβ probes to perform hybridization. Given the specific requirements of the two-step PCR detection system and specificity of the Vβ-Dβ-Jβ primers and probes, the identified DNA sequences would derive from specific TCR Vβ chains and represent either identical or similar to Vβ-Dβ-Jβ sequences of interest.

The results indicated that only one Vβ-Dβ-Jβ oligonucleotide primer (MS1-E2.6, Vβ13.1-LGRAGLTY) detected complementary TCR Vβ13.1 DNA sequence in 15 of 48 (31%) PBMC specimens obtained from different patients with MS. Thus, the finding indicates the presence of MBP83–99 T cells expressing Vβ13.1-LGRAGLTY in these patients with MS. Under similar experimental conditions, the same primer also detected corresponding DNA sequence in 5 of 20 (25%) PBMC specimens derived from healthy individuals. The remaining 13 Vβ-Dβ-Jβ primers failed to identify any sequence signals in the same panel of PBMC specimens. The results were reproducible in three separate experiments. The identified DNA products amplified by the E2.6 primer originated from T cells expressing Vβ013.1 because a Vβ13.1-specific primer was used in the first PCR for amplification.

Furthermore, the identified Vβ13.1-LGRAGLTY sequence was also amplified in 13 of 24 (54%) short-term MBP83–99 T cell lines generated from five patients with MS (MS-35, MS36 and MS39) whose PBMC specimens were shown to contain the Vβ13.1-LGRAGLTY sequence. The results thus confirmed that the Vβ13.1-LGRAGLTY DNA sequence detected in the PBMC specimens originated from T cells recognizing MBP83–99. The finding also suggests that MBP83–99 T cells expressing the Vβ13.1-LGRAGLTY sequence represent all or the majority of MBP83–99 T cell lines found in some patients with MS.

A combined PCR-DNA hybridization detection system where Vβ-Dβ-Jβ sequences were used as a fingerprint provided a powerful tool in tracing antigen-specific T cells by detecting identical Vβ-Dβ-Jβ junctional sequences. The high specificity and sensitivity of the detection system allowed the identification of specific Vβ-Dβ-Jβ sequences in peripheral blood T cells. The present study demonstrated for the first time that a common subset of Vβ13.1 T cells that recognize the immunodominant 83–99 peptide of MBP and uniformly express an identical Vβ-Dβ-Jβ sequence is present in approximately 30% of patients with MS. The conclusion is made based on step-wise experiments described herein. First, the identical DNA sequence (Vβ13.1-LGRAGLTY) was found among independent MBP83–99 T cell clones derived from different patients with MS. Second, the sequence was identified in cDNA products amplified from TCR Vβ13.1 of PBMC specimens obtained from different patients with MS. Third, the DNA sequence was detected in short-term independent MBP83–99 T cell lines generated from PBMC specimens that were shown to contain the Vβ13.1-LGRAGLTY sequence. MBP83–99 T cells expressing the Vβ13.1-LGRAGLTY sequence seem to represent all or the majority of the MBP83–99 T cell lines generated from some patients with MS. Finally, the presence of Vβ13.1-LGRAGLTY sequence in PBMC specimens was confirmed by recombinant DNA cloning and direct DNA sequencing.

Furthermore, it is not surprising that MBP83–99 T cells expressing the common Vβ3.1-LGRAGLTY sequence are also present in some healthy individuals. Studies reported so far indicate that MBP-reactive T cells, including T cells recognizing the immunodominant 83–99 peptide, are also present in some healthy individuals (Zhang 1994, Ota 1990). However, there is a functional difference that these T cells undergo in vivo activation and clonal expansion in patients with MS, as opposed to healthy individuals (Zhang 1994).

These Vβ3.1 MBP83–99 T cells sharing the common Vβ-DβJβ sequence may represent a significant fraction of MBP83–99 T cells found in some patients with MS. This possibility is supported by the observation that the Vβ13.1-LGRAGLTY sequence was present in 40% of short-term MBP83–99 T cell lines generated from patients with MS after two stimulation cycles.

The identified common Vβ-Dβ-Jβ sequence may be used as a specific marker in a quantitative PCR detection system to detect a common subset of MBP83–99 T cells in the blood and cerebrospinal fluid in a large group of MS patients for the purpose of monitoring in vivo clonal expansion and in vivo activity potentially associated with the disease. This method will be superior to conventional cell culture-based assays because in vitro selection and expansion of MBP-reactive T cells are often hampered by various inhibitory factors inherent in cell culture. This is consistent with a recent study where the frequency of MBP-reactive T cells was found to be surprisingly high in patients with MS when direct ex vivo analysis was employed to quantify MBP-reactive T cells (Hafler as last author JEM 1997).

Furthermore, synthetic peptides corresponding to the TCR have been shown to induce anti-idiotypic T cell responses to MBP-reactive T cells in patients with MS (Chou et al, J. I.). Therefore, a TCR peptide containing a common CDR3 sequence may be of great potential in eliciting anti-idiotypic T cells to suppress a specific subset of MBP-reactive T cells in a group of patients whose MBP83–99 T cells bear the common CDR3 sequence motif. Immunization with such a common CDR3 peptide would be advantageous over CDR2 peptides or individual-dependent CDR3 peptides as a potential treatment procedure in patients with MS (Vandenbark 1996).

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. An oligonucleotide of about 15 to 30 nucleotides in length, comprising at least 10 contiguous nucleotides of SEQ ID NO:1, or comprising at least 10 contiguous nucleotides of the complement of SEQ ID NO:1.

2. The oligonucleotide of claim 1, which comprises at least 15 contiguous nucleotides of SEQ ID NO:1, or comprising at least 10 contiguous nucleotides of the complement of SEQ ID NO:1.

3. The oligonucleotide of claim 1, which comprises the sequence of SEQ ID NO:1, or comprising at least 10 contiguous nucleotides of the complement of SEQ ID NO:1.

4. A primer pair, comprising:
(a) a first primer of about 15 to 30 nucleotides in length, comprising at least 10 contiguous nucleotides of SEQ ID NO:1, or the nucleic acid complementary thereto; and
(b) a second primer comprising a nucleic acid of about 15 and 30 nucleotides in length that does not comprise the sequence of (a) and is found in the region from Vβ to Jβ of the Vβ13.1 gene in T cell receptor T cells, wherein the sequences of said first and second primers are not found on the same strand of the T cell receptor gene.

5. The primer pair of claim 4, wherein the second primer comprises SEQ ID NO:2.

6. An oligonucleotide probe comprising:
(a) an oligonucleotide of about 10 to 30 nucleotides in length, comprising at least 10 contiguous nucleotides of SEQ ID NO:1, or comprising at least 10 contiguous nucleotides of the complement of SEQ ID NO:1 and
(b) a labeling moiety.

7. The oligonucleotide probe of claim 6, wherein the labeling moiety is selected from $^{32}$P or digoxingenin.

8. A method of detecting MBP83–99 Vβ13.1 T cells expressing a T cell receptor LGRAGLTY motif, comprising:
(a) obtaining a nucleic acid sample from MBP83–99 Vβ13.1 T cells;
(b) contacting the nucleic acid sample with a primer pair selected from:
(i) a first oligonucleotide of about 15 to 30 nucleotides in length, comprising at least 10 contiguous nucleotides of SEQ ID NO:1, or comprising at least 10 contiguous nucleotides of the complement of SEQ ID NO:1; and
(ii) a second oligonucleotide of about 15 and 30 nucleotides in length that does not comprise the sequence of the first oligonucleotide and is found in the region from Vβ to Jβ of the Vβ13.1 gene in T cell receptor T cells,
wherein the sequences of the first and second oligonucleotides are not found on the same strand of the T cell receptor gene; and
(c) detecting the presence of the nucleic acid encoding the LGRAGLTY motif.

9. The method of claim 8, wherein the second primer comprises SEQ ID NO:2.

10. The method according to claim 8, wherein a fragment of the nucleic acid sample is amplified by polymerase chain reaction (PCR).

11. The method according to claim 10, wherein the detection step comprises probing with an oligonucleotide probe comprising:
(a) an oligonucleotide, which comprises the sequence of SEQ ID NO:1, or the nucleic acid complementary thereto; and,
(b) a labeling moiety.

12. The method according to claim 10, wherein the detection step comprises autoradiography.

13. A test kit comprising a first oligonucleotide of about 15–30 nucleotides in length:
said first oligonucleotide comprising at least 10 contiguous nucleotides of SEQ ID NO:1, or comprising at least 10 contiguous nucleotides of the complement of SEQ ID NO:1.

14. The test kit of claim 13, further comprising: a second oligonucleotide of about 15 and 30 nucleotides in length that does not comprise the sequence of said first oligonucleotide and is found in the region from Vβ to Jβ of the Vβ13.1 gene in T cell receptor T cells, wherein the sequences of the first and second oligonucleotides are not found on the same strand of the T cell receptor gene.

15. The test kit of claim 14, wherein the second primer comprises SEQ ID NO:2.

16. The test kit of claim 13, further comprising a labeling moiety, wherein the labeling moiety is selected from $^{32}$P or digoxingenin.

17. A method of monitoring an autoimmune disease, comprising:
(A) obtaining MBP83–99 Vβ13.1 T cells from a human;
(B) detecting the presence of a nucleic acid encoding a LGRAGLTY motif by
(i) obtaining a nucleic acid sample from MBP83–99 Vβ13.1 T cells;
(ii) contacting the nucleic acid sample with a primer pair selected from:
(a) a first oligonucleotide of about 15 to 30 nucleotides in length, comprising at least 10 contiguous nucleotides of SEQ ID NO:1, or comprising at least 10 contiguous nucleotides of the complement of SEQ ID NO:1; and
(b) a second oligonucleotide of about 15 and 30 nucleotides in length that does not comprise the sequence of said first oligonucleotide and is found in the region from Vβ to Jβ of the Vβ13.1 gene in T cell receptor T cells,
wherein the sequences of said first and second oligonucleotides are not found on the same strand of the T cell receptor gene; and
(c) detecting the presence of the nucleic acid encoding the LGRAGLTY motif; and, if the nucleic acid is detected,
(C) quantifying the amount of the nucleic acid.

18. The method of 17, wherein the second primer comprises SEQ ID NO:2.

* * * * *

SEQUENCE LISTING

```
<160> NUMBER OF SEQ ID NOS: 77

<210> SEQ ID NO 1
<211> LENGTH: 24
<212> TYPE: DNA
<213> ORGANISM: SYNTHETIC

<400> SEQUENCE: 1
ctagggcggg cgggactcac ctac                                            24

<210> SEQ ID NO 2
<211> LENGTH: 400
<212> TYPE: DNA
<213> ORGANISM: Homo sapiens

<400> SEQUENCE: 2
catgtctccg ataacccaga ggatttcccg ctcaggctgc tgtcggctgc tccctcccag     60
acatctgtgt acttctgtgc cagcagccta gggcgggcgg gactcaccta cgagcagtac    120
ttcgggccgg gcaccaggct cacggtcaca gaggacctga aaacgtgtt cccacccgag     180 gtcgctgtgt ttgagccatc agaagcagag atctcccaca cccaaaaggc cacactggta    240
tgcctggcca caggcttcta ccccgaccac gtggagctga gctggtgggt gaatgggaag    300
gaggtgcaca gtgggggtcag cacagacccg cagcccctca aggagcagcc cgccctcaat    360
gactccagat actgcctgag cagccgcctg agggtctcgg                          400

<210> SEQ ID NO 3
<211> LENGTH: 8
<212> TYPE: PRT
<213> ORGANISM: Homo sapiens

<400> SEQUENCE: 3

Leu Gly Arg Ala Gly Leu Thr Tyr
 1               5

<210> SEQ ID NO 4
<211> LENGTH: 30
<212> TYPE: PRT
<213> ORGANISM: Homo sapiens
```

```
<400> SEQUENCE: 4

Tyr Phe Cys Ala Leu Ser Arg Gly Gly Ser Asn Tyr Lys Leu Thr Phe
 1               5                  10                  15
Gly Lys Gly Thr Leu Leu Thr Val Asn Pro Asn Ile Gln Asn
            20                  25                  30

<210> SEQ ID NO 5
<211> LENGTH: 90
<212> TYPE: DNA
<213> ORGANISM: Homo sapiens

<400> SEQUENCE: 5
tacttctgtg ctctgagtag gggaggtagc aactataaac tgacatttgg aaaaggaact    60
ctcttaaccg tgaatccaaa tatccagaac                                    90

<210> SEQ ID NO 6
<211> LENGTH: 30
<212> TYPE: PRT
<213> ORGANISM: Homo sapiens

<400> SEQUENCE: 6

Tyr Tyr Cys Ala Leu Lys Arg Asn Phe Gly Asn Glu Lys Leu Thr Phe
 1               5                  10                  15
Gly Thr Gly Thr Arg Leu Thr Ile Ile Pro Asn Ile Gln Asn
            20                  25                  30

<210> SEQ ID NO 7
<211> LENGTH: 90
<212> TYPE: DNA
<213> ORGANISM: Homo sapiens

<400> SEQUENCE: 7
tattactgtg ctctaaaaag aaactttgga aatgagaaat taacctttgg gactggaaca    60
agactcacca tcatacccaa tatccagaac                                    90

<210> SEQ ID NO 8
<211> LENGTH: 30
<212> TYPE: PRT
<213> ORGANISM: Homo sapiens

<400> SEQUENCE: 8

Tyr Phe Cys Ala Ala Ser Pro Gly Gly Ser Asn Tyr Lys Leu Thr Phe
 1               5                  10                  15
Gly Lys Gly Thr Leu Leu Thr Val Asn Pro Asn Ile Gln Asn
            20                  25                  30

<210> SEQ ID NO 9
<211> LENGTH: 90
<212> TYPE: DNA
<213> ORGANISM: Homo sapiens

<400> SEQUENCE: 9
tacttctgtg cagcaagccc cggaggtagc aactataaac tgacatttgg aaaaggaact    60
ctcttaaccg tgaatccaaa tatccagaac                                    90

<210> SEQ ID NO 10
<211> LENGTH: 30
<212> TYPE: PRT
<213> ORGANISM: Homo sapiens

<400> SEQUENCE: 10
```

Tyr Phe Cys Ala Ala Met Gly Asp Phe Gly Asn Glu Lys Leu Thr Phe
 1               5                  10                  15

Gly Thr Gly Thr Arg Leu Thr Ile Ile Pro Asn Ile Gln Asn
            20                  25                  30

<210> SEQ ID NO 11
<211> LENGTH: 90
<212> TYPE: DNA
<213> ORGANISM: Homo sapiens

<400> SEQUENCE: 11
tacttctgtg cagcaatggg ggactttgga aatgagaaat taacctttgg gactggaaca      60
agactcacca tcatacccaa tatccagaac                                       90

<210> SEQ ID NO 12
<211> LENGTH: 30
<212> TYPE: PRT
<213> ORGANISM: Homo sapiens

<400> SEQUENCE: 12

Tyr Phe Cys Ala Ala Met Gly Asp Phe Gly Asn Glu Lys Leu Thr Phe
 1               5                  10                  15

Gly Thr Gly Thr Arg Leu Thr Ile Ile Pro Asn Ile Gln Asn
            20                  25                  30

<210> SEQ ID NO 13
<211> LENGTH: 90
<212> TYPE: DNA
<213> ORGANISM: Homo sapiens

<400> SEQUENCE: 13
tacttctgtg cagcaatggg ggactttgga aatgagaaat taacctttgg gactggaaca      60
agactcacca tcatacccaa tatccagaac                                       90

<210> SEQ ID NO 14
<211> LENGTH: 30
<212> TYPE: PRT
<213> ORGANISM: Homo sapiens

<400> SEQUENCE: 14

Tyr Phe Cys Ala Ala Met Gly Asp Phe Gly Asn Glu Lys Leu Thr Phe
 1               5                  10                  15

Gly Thr Gly Thr Arg Leu Thr Ile Ile Pro Asn Ile Gln Asn
            20                  25                  30

<210> SEQ ID NO 15
<211> LENGTH: 90
<212> TYPE: DNA
<213> ORGANISM: Homo sapiens

<400> SEQUENCE: 15
tacttctgtg cagcaatggg ggactttgga aatgagaaat taacctttgg gactggaaca      60
agactcacca tcatacccaa tatccagaac                                       90

<210> SEQ ID NO 16
<211> LENGTH: 32
<212> TYPE: PRT
<213> ORGANISM: Homo sapiens

<400> SEQUENCE: 16

Tyr Phe Cys Ala Leu Ser Val Ala Gly Gly Thr Ser Tyr Gly Lys Leu
 1               5                  10                  15
Thr Phe Gly Gln Gly Thr Ile Leu Thr Val His Pro Asn Ile Gln Asn
                20                  25                  30

<210> SEQ ID NO 17
<211> LENGTH: 96
<212> TYPE: DNA
<213> ORGANISM: Homo sapiens

<400> SEQUENCE: 17
tacttctgtg ctctgagcgt tgctggtggt actagctatg gaaagctgac atttggacaa      60
gggaccatct tgactgtcca tccaaatatc cagaac                                96

<210> SEQ ID NO 18
<211> LENGTH: 33
<212> TYPE: PRT
<213> ORGANISM: Homo sapiens

<400> SEQUENCE: 18

Tyr Tyr Cys Leu Val Gly Asp Ala Val Arg Pro Gly Gly Gly Asn Lys
 1               5                  10                  15
Leu Thr Phe Gly Thr Gly Thr Gln Leu Lys Val Glu Leu Asn Ile Gln
                20                  25                  30
Asn

<210> SEQ ID NO 19
<211> LENGTH: 99
<212> TYPE: DNA
<213> ORGANISM: Homo sapiens

<400> SEQUENCE: 19
tactactgcc tcgtgggtga cgccgtgagg ccgggaggag gaaacaaact cacctttggg      60
acaggcactc agctaaaagt ggaactcaat atccagaac                             99

<210> SEQ ID NO 20
<211> LENGTH: 33
<212> TYPE: PRT
<213> ORGANISM: Homo sapiens

<400> SEQUENCE: 20

Tyr Tyr Cys Leu Val Gly Asp Ala Val Arg Pro Gly Gly Gly Asn Lys
 1               5                  10                  15
Leu Thr Phe Gly Thr Gly Thr Gln Leu Lys Val Glu Leu Asn Ile Gln
                20                  25                  30
Asn

<210> SEQ ID NO 21
<211> LENGTH: 99
<212> TYPE: DNA
<213> ORGANISM: Homo sapiens

<400> SEQUENCE: 21
tactactgcc tcgtgggtga cgccgtgagg ccgggaggag gaaacaaact cacctttggg      60
acaggcactc agctaaaagt ggaactcaat atccagaac                             99

<210> SEQ ID NO 22
<211> LENGTH: 29
<212> TYPE: PRT
<213> ORGANISM: Homo sapiens -continued

<400> SEQUENCE: 22

Tyr Phe Cys Ala Thr Asp Ala Gly Gly Thr Tyr Lys Tyr Ile Phe Gly
 1               5                  10                  15
Thr Gly Thr Arg Leu Lys Val Leu Ala Asn Ile Gln Asn
            20                  25

<210> SEQ ID NO 23
<211> LENGTH: 87
<212> TYPE: DNA
<213> ORGANISM: Homo sapiens

<400> SEQUENCE: 23
tacttctgtg ctacggacgc aggaggaacc tacaaataca tctttggaac aggcaccagg    60
ctgaaggttt tagcaaatat ccagaac                                        87

<210> SEQ ID NO 24
<211> LENGTH: 27
<212> TYPE: PRT
<213> ORGANISM: Homo sapiens

<400> SEQUENCE: 24

Tyr Tyr Cys Leu Val Gly Asp Ile Asp Asp Met Arg Phe Gly Ala Gly
 1               5                  10                  15
Thr Arg Leu Thr Val Lys Pro Asn Ile Gln Asn
            20                  25

<210> SEQ ID NO 25
<211> LENGTH: 81
<212> TYPE: DNA
<213> ORGANISM: Homo sapiens

<400> SEQUENCE: 25
tactactgcc tcgtgggtga catcgatgac atgcgctttg gagcagggac cagactgaca    60
gtaaaaccaa atatccagaa c                                              81

<210> SEQ ID NO 26
<211> LENGTH: 28
<212> TYPE: PRT
<213> ORGANISM: Homo sapiens

<400> SEQUENCE: 26

Tyr Phe Cys Ala Thr Ser Val Asn Thr Asp Lys Leu Ile Phe Gly Thr
 1               5                  10                  15
Gly Thr Arg Leu Gln Val Phe Pro Asn Ile Gln Asn
            20                  25

<210> SEQ ID NO 27
<211> LENGTH: 84
<212> TYPE: DNA
<213> ORGANISM: Homo sapiens

<400> SEQUENCE: 27
tacttctgtg ctacatcggt taacaccgac aagctcatct ttgggactgg gaccagatta    60
caagtctttc caaatatcca gaac                                           84

<210> SEQ ID NO 28
<211> LENGTH: 35
<212> TYPE: PRT
<213> ORGANISM: Homo sapiens

<400> SEQUENCE: 28

Tyr Phe Cys Ala Ser Ser Gln Asp Arg Phe Trp Gly Gly Thr Val Asn
1               5                   10                  15

Thr Glu Ala Phe Phe Gly Gln Gly Thr Arg Leu Thr Val Val Glu Asp
            20                  25                  30

Leu Asn Lys
        35

<210> SEQ ID NO 29
<211> LENGTH: 105
<212> TYPE: DNA
<213> ORGANISM: Homo sapiens

<400> SEQUENCE: 29
tatttctgtg ccagcagcca agatcgtttt tgggggggga cggtgaacac tgaagctttc     60
tttggacaag gcaccagact cacagttgta gaggacctga acaag                    105

<210> SEQ ID NO 30
<211> LENGTH: 28
<212> TYPE: PRT
<213> ORGANISM: Homo sapiens

<400> SEQUENCE: 30

Tyr Phe Cys Ala Ser Ser Ala Met Gly Glu Thr Gln Tyr Phe Gly Pro
1               5                   10                  15

Gly Thr Arg Leu Leu Val Leu Glu Asp Leu Lys Asn
            20                  25

<210> SEQ ID NO 31
<211> LENGTH: 84
<212> TYPE: DNA
<213> ORGANISM: Homo sapiens

<400> SEQUENCE: 31
tatttctgtg ccagcagcgc tatgggagag acccagtact cgggccagg cacgcggctc      60 ctggtgctcg aggacctgaa aaac                                            84

<210> SEQ ID NO 32
<211> LENGTH: 32
<212> TYPE: PRT
<213> ORGANISM: Homo sapiens

<400> SEQUENCE: 32

Tyr Phe Cys Ala Ser Ser Leu Gly Arg Ala Gly Leu Thr Tyr Glu Gln
1               5                   10                  15

Tyr Phe Gly Pro Gly Thr Arg Leu Thr Val Thr Glu Asp Leu Lys Asn
            20                  25                  30

<210> SEQ ID NO 33
<211> LENGTH: 96
<212> TYPE: DNA
<213> ORGANISM: Homo sapiens

<400> SEQUENCE: 33
tacttctgtg ccagcagcct agggcgggcg ggactcacct acgagcagta cttcgggccg     60
ggcaccaggc tcacggtcac agaggacctg aaaaac                               96

<210> SEQ ID NO 34
<211> LENGTH: 32
<212> TYPE: PRT

<213> ORGANISM: Homo sapiens

<400> SEQUENCE: 34

Tyr Phe Cys Ala Ser Ser Leu Gly Arg Ala Gly Leu Thr Tyr Glu Gln
1               5                   10                  15

Tyr Phe Gly Pro Gly Thr Arg Leu Thr Val Thr Glu Asp Leu Lys Asn
            20                  25                  30

<210> SEQ ID NO 35
<211> LENGTH: 96
<212> TYPE: DNA
<213> ORGANISM: Homo sapiens

<400> SEQUENCE: 35
tacttctgtg ccagcagcct agggcgggcg ggactcacct acgagcagta cttcgggccg     60
ggcaccaggc tcacggtcac agaggacctg aaaaac                               96

<210> SEQ ID NO 36
<211> LENGTH: 31
<212> TYPE: PRT
<213> ORGANISM: Homo sapiens

<400> SEQUENCE: 36

Phe Cys Ala Ser Ser Leu Gly Arg Ala Gly Leu Thr Tyr Glu Gln Tyr
1               5                   10                  15

Phe Gly Pro Gly Thr Arg Leu Thr Val Thr Glu Asp Leu Lys Asn
            20                  25                  30

<210> SEQ ID NO 37
<211> LENGTH: 96
<212> TYPE: DNA
<213> ORGANISM: Homo sapiens

<400> SEQUENCE: 37
tacttctgtg ccagcagcct agggcgggcg ggactcacct acgagcagta cttcgggccg     60
ggcaccaggc tcacggtcac agaggacctg aaaaac                               96

<210> SEQ ID NO 38
<211> LENGTH: 32
<212> TYPE: PRT
<213> ORGANISM: Homo sapiens

<400> SEQUENCE: 38

Tyr Phe Cys Ala Ser Ser Leu Gly Arg Ala Gly Leu Thr Tyr Glu Gln
1               5                   10                  15

Tyr Phe Gly Pro Gly Thr Arg Leu Thr Val Thr Glu Asp Leu Lys Asn
            20                  25                  30

<210> SEQ ID NO 39
<211> LENGTH: 96
<212> TYPE: DNA
<213> ORGANISM: Homo sapiens

<400> SEQUENCE: 39
tacttctgtg ccagcagcct agggcgggcg ggactcacct acgagcagta cttcgggccg     60
ggcaccaggc tcacggtcac agaggacctg aaaaac                               96

<210> SEQ ID NO 40
<211> LENGTH: 29
<212> TYPE: PRT
<213> ORGANISM: Homo sapiens

<400> SEQUENCE: 40

Tyr Phe Cys Ala Ser Ser Pro Thr Val Asn Tyr Gly Tyr Thr Phe Gly
 1               5                  10                  15
Ser Gly Thr Arg Leu Thr Val Val Glu Asp Leu Asn Lys
            20                  25

<210> SEQ ID NO 41
<211> LENGTH: 87
<212> TYPE: DNA
<213> ORGANISM: Homo sapiens

<400> SEQUENCE: 41
tatttctgtg ccagcagccc gacagttaac tatggctaca ccttcggttc ggggaccagg    60
ttaaccgttg tagaggacct gaacaag                                       87

<210> SEQ ID NO 42
<211> LENGTH: 32
<212> TYPE: PRT
<213> ORGANISM: Homo sapiens

<400> SEQUENCE: 42

Tyr Phe Cys Ala Ser Ser Tyr Ser Ile Arg Gly Gln Gly Asn Glu Gln
 1               5                  10                  15
Tyr Phe Gly Pro Gly Thr Arg Leu Thr Val Thr Glu Asp Leu Lys Asn
            20                  25                  30

<210> SEQ ID NO 43
<211> LENGTH: 96
<212> TYPE: DNA
<213> ORGANISM: Homo sapiens

<400> SEQUENCE: 43
tacttctgtg ccagcagtta ctcgattagg ggacagggta acgagcagta cttcgggccg    60
ggcaccaggc tcacggtcac agaggacctg aaaaac                              96

<210> SEQ ID NO 44
<211> LENGTH: 32
<212> TYPE: PRT
<213> ORGANISM: Homo sapiens

<400> SEQUENCE: 44

Tyr Phe Cys Ala Ser Ser Tyr Ser Ile Arg Gly Gln Gly Asn Glu Gln
 1               5                  10                  15
Tyr Phe Arg Pro Gly Thr Arg Leu Thr Val Thr Glu Asp Leu Lys Asn
            20                  25                  30

<210> SEQ ID NO 45
<211> LENGTH: 96
<212> TYPE: DNA
<213> ORGANISM: Homo sapiens

<400> SEQUENCE: 45
tacttctgtg ccagcagtta ctcgattagg ggacagggta acgagcagta cttccggccg    60
ggcaccaggc tcacggtcac agaggacctg aaaaac                              96

<210> SEQ ID NO 46
<211> LENGTH: 29
<212> TYPE: PRT
<213> ORGANISM: Homo sapiens

<400> SEQUENCE: 46

Tyr Leu Cys Ala Ser Ser Gln Asp Arg Val Ala Pro Gln Tyr Phe Gly
 1               5                  10                  15
Pro Gly Thr Arg Leu Leu Val Leu Glu Asp Leu Lys Asn
            20                  25

<210> SEQ ID NO 47
<211> LENGTH: 87
<212> TYPE: DNA
<213> ORGANISM: Homo sapiens

<400> SEQUENCE: 47
tatctctgtg ccagcagcca agatcgggtt gcgccacagt acttcgggcc aggcacgcgg     60
ctcctggtgc tcgaggacct gaaaaac                                         87

<210> SEQ ID NO 48
<211> LENGTH: 31
<212> TYPE: PRT
<213> ORGANISM: Homo sapiens

<400> SEQUENCE: 48

Tyr Leu Cys Ala Ser Ser Thr Arg Gln Gly Pro Gln Glu Thr Gln Tyr
 1               5                  10                  15
Phe Gly Pro Gly Thr Arg Leu Leu Val Leu Glu Asp Leu Lys Asn
            20                  25                  30

<210> SEQ ID NO 49
<211> LENGTH: 93
<212> TYPE: DNA
<213> ORGANISM: Homo sapiens

<400> SEQUENCE: 49
tatctctgtg ccagtagtac ccggcaagga cctcaagaga cccagtactt cgggccaggc     60
acgcggctcc tggtgctcga ggacctgaaa aac                                  93

<210> SEQ ID NO 50
<211> LENGTH: 30
<212> TYPE: PRT
<213> ORGANISM: Homo sapiens

<400> SEQUENCE: 50

Tyr Leu Cys Ala Ser Ser Leu Gly Gln Gly Ala Tyr Glu Gln Tyr Phe
 1               5                  10                  15
Gly Pro Gly Thr Arg Leu Thr Val Thr Glu Asp Leu Lys Asn
            20                  25                  30

<210> SEQ ID NO 51
<211> LENGTH: 90
<212> TYPE: DNA
<213> ORGANISM: Homo sapiens

<400> SEQUENCE: 51
tatctctgtg ccagcagctt aggacagggg gcttacgagc agtacttcgg gccgggcacc     60
aggctcacgg tcacagagga cctgaaaaac                                      90

<210> SEQ ID NO 52
<211> LENGTH: 30
<212> TYPE: PRT
<213> ORGANISM: Homo sapiens

<400> SEQUENCE: 52

Tyr Leu Cys Ala Ser Ser Leu Gly Gln Gly Ala Tyr Glu Gln Tyr Phe
 1               5                  10                  15

Gly Pro Gly Thr Arg Leu Thr Val Thr Glu Asp Leu Lys Asn
            20                  25                  30

<210> SEQ ID NO 53
<211> LENGTH: 90
<212> TYPE: DNA
<213> ORGANISM: Homo sapiens

<400> SEQUENCE: 53
tatctctgtg ccagcagctt aggacagggg gcttacgagc agtacttcgg gccgggcacc      60
aggctcacgg tcacagagga cctgaaaaac                                       90

<210> SEQ ID NO 54
<211> LENGTH: 30
<212> TYPE: PRT
<213> ORGANISM: Homo sapiens

<400> SEQUENCE: 54

Tyr Leu Cys Ala Ser Ser Leu Gly Gln Gly Ala Tyr Glu Gln Tyr Phe
 1               5                  10                  15

Gly Pro Gly Thr Arg Leu Thr Val Thr Glu Asp Leu Lys Asn
            20                  25                  30

<210> SEQ ID NO 55
<211> LENGTH: 90
<212> TYPE: DNA
<213> ORGANISM: Homo sapiens

<400> SEQUENCE: 55
tatctctgtg ccagcagctt aggacagggg gcttacgagc agtacttcgg gccgggcacc      60
aggctcacgg tcacagagga cctgaaaaac                                       90

<210> SEQ ID NO 56
<211> LENGTH: 29
<212> TYPE: PRT
<213> ORGANISM: Homo sapiens

<400> SEQUENCE: 56

Tyr Phe Cys Ala Ser Ser Leu Gln Val Tyr Ser Pro Leu His Phe Gly
 1               5                  10                  15

Asn Gly Thr Arg Leu Thr Val Thr Glu Asp Leu Asn Lys
            20                  25

<210> SEQ ID NO 57
<211> LENGTH: 87
<212> TYPE: DNA
<213> ORGANISM: Homo sapiens

<400> SEQUENCE: 57
tacttctgtg ccagcagttt acaagtgtat tcacccctcc actttgggaa cgggaccagg      60
ctcactgtga cagaggacct gaacaag                                          87

<210> SEQ ID NO 58
<211> LENGTH: 31
<212> TYPE: PRT
<213> ORGANISM: Homo sapiens

<400> SEQUENCE: 58

```
Tyr Phe Cys Ala Ile Ser Glu Ser Ile Gly Thr Gly Thr Glu Ala Phe
 1               5                  10                  15

Phe Gly Gln Gly Thr Arg Leu Thr Val Val Glu Asp Leu Asn Lys
                 20                  25                  30
```

<210> SEQ ID NO 59
<211> LENGTH: 93
<212> TYPE: DNA
<213> ORGANISM: Homo sapiens

<400> SEQUENCE: 59

```
tacttctgtg ccatcagtga gtcgattggt acgggaactg aagctttctt tggacaaggc      60
accagactca cagttgtaga ggacctgaac aag                                   93
```

<210> SEQ ID NO 60
<211> LENGTH: 31
<212> TYPE: PRT
<213> ORGANISM: Homo sapiens

<400> SEQUENCE: 60

```
Tyr Phe Cys Ala Ile Ser Glu Ser Ile Gly Thr Gly Thr Glu Ala Phe
 1               5                  10                  15

Phe Gly Gln Gly Thr Arg Leu Thr Val Val Glu Asp Leu Asn Lys
                 20                  25                  30
```

<210> SEQ ID NO 61
<211> LENGTH: 93
<212> TYPE: DNA
<213> ORGANISM: Homo sapiens

<400> SEQUENCE: 61

```
tacttctgtg ccatcagtga gtcgattggt acgggaactg aagctttctt tggacaaggc      60
accagactca cagttgtaga ggacctgaac aag                                   93
```

<210> SEQ ID NO 62
<211> LENGTH: 28
<212> TYPE: PRT
<213> ORGANISM: Homo sapiens

<400> SEQUENCE: 62

```
Tyr Leu Cys Ala Ser Arg Asp Arg Ser Tyr Glu Gln Tyr Phe Gly Pro
 1               5                  10                  15

Gly Thr Arg Leu Thr Val Thr Glu Asp Leu Lys Asn
                 20                  25
```

<210> SEQ ID NO 63
<211> LENGTH: 84
<212> TYPE: DNA
<213> ORGANISM: Homo sapiens

<400> SEQUENCE: 63

```
tacctctgtg ccagccggga caggtcctac gagcagtact tcgggccggg caccaggctc      60
acggtcacag aggacctgaa aaac                                             84
```

<210> SEQ ID NO 64
<211> LENGTH: 31
<212> TYPE: PRT
<213> ORGANISM: Homo sapiens

<400> SEQUENCE: 64

Tyr Phe Cys Ala Ile Ser Glu Gly Ser Ser Ser Gly Asn Thr Ile Tyr
```

```
            1               5              10              15
Phe Gly Glu Gly Ser Trp Leu Thr Val Val Glu Asp Leu Asn Lys
                     20              25              30
```

<210> SEQ ID NO 65
<211> LENGTH: 93
<212> TYPE: DNA
<213> ORGANISM: Homo sapiens

<400> SEQUENCE: 65

```
tacttctgtg ccatcagtga ggggtccagc tctggaaaca ccatatattt tggagaggga      60
agttggctca ctgttgtaga ggacctgaac aag                                   93
```

<210> SEQ ID NO 66
<211> LENGTH: 26
<212> TYPE: PRT
<213> ORGANISM: Homo sapiens

<400> SEQUENCE: 66

```
Phe Tyr Ile Cys Ser Ala Ile Asp Gly Tyr Thr Phe Gly Ser Gly Thr
 1               5                  10                  15
Arg Leu Thr Val Val Glu Asp Leu Asn Lys
                20                  25
```

<210> SEQ ID NO 67
<211> LENGTH: 78
<212> TYPE: DNA
<213> ORGANISM: Homo sapiens

<400> SEQUENCE: 67

```
ttctacatct gcagtgctat agacggctac accttcggtt cggggaccag gttaaccgtt      60
gtagaggacc tgaacaag                                                    78
```

<210> SEQ ID NO 68
<211> LENGTH: 21
<212> TYPE: DNA
<213> ORGANISM: Homo sapiens

<400> SEQUENCE: 68

```
agcagccaag atcgttttg g                                                 21
```

<210> SEQ ID NO 69
<211> LENGTH: 24
<212> TYPE: DNA
<213> ORGANISM: Homo sapiens

<400> SEQUENCE: 69

```
ctagggcggg cgggactcac ctac                                             24
```

<210> SEQ ID NO 70
<211> LENGTH: 24
<212> TYPE: DNA
<213> ORGANISM: Homo sapiens

<400> SEQUENCE: 70

```
ctagggcggg cgggactcac ctac                                             24
```

<210> SEQ ID NO 71
<211> LENGTH: 24
<212> TYPE: DNA
<213> ORGANISM: Homo sapiens -continued

```
<400> SEQUENCE: 71
tactcgatta ggggacaggg taac                                              24

<210> SEQ ID NO 72
<211> LENGTH: 18
<212> TYPE: DNA
<213> ORGANISM: Homo sapiens

<400> SEQUENCE: 72
caagatcggg ttgcgcca                                                     18

<210> SEQ ID NO 73
<211> LENGTH: 24
<212> TYPE: DNA
<213> ORGANISM: Homo sapiens

<400> SEQUENCE: 73
acccggcaag gacctcaaga gacc                                              24

<210> SEQ ID NO 74
<211> LENGTH: 18
<212> TYPE: DNA
<213> ORGANISM: Homo sapiens

<400> SEQUENCE: 74
agcttaggac aggggct                                                      18

<210> SEQ ID NO 75
<211> LENGTH: 18
<212> TYPE: DNA
<213> ORGANISM: Homo sapiens

<400> SEQUENCE: 75
gccagccggg acaggtcc                                                     18

<210> SEQ ID NO 76
<211> LENGTH: 18
<212> TYPE: DNA
<213> ORGANISM: Homo sapiens

<400> SEQUENCE: 76
gagtagattg gtacggga                                                     18

<210> SEQ ID NO 77
<211> LENGTH: 21
<212> TYPE: DNA
<213> ORGANISM: Homo sapiens

<400> SEQUENCE: 77
tacatctgaa gtgctataga c                                                 21
```